United States Patent
Haasl et al.

(10) Patent No.: US 11,278,720 B2
(45) Date of Patent: Mar. 22, 2022

(54) DELIVERY DEVICES AND METHODS FOR LEADLESS CARDIAC DEVICES

(71) Applicant: CARDIAC PACEMAKERS, INC., St. Paul, MN (US)

(72) Inventors: Benjamin J. Haasl, Forest Lake, MN (US); Brian L. Schmidt, White Bear Lake, MN (US)

(73) Assignee: CARDIAC PACEMAKERS, INC., St. Paul, MN (US)

(*) Notice: Subject to any disclaimer, the term of this patent is extended or adjusted under 35 U.S.C. 154(b) by 963 days.

(21) Appl. No.: 14/919,233

(22) Filed: Oct. 21, 2015

(65) Prior Publication Data

US 2016/0114156 A1 Apr. 28, 2016

Related U.S. Application Data

(60) Provisional application No. 62/067,074, filed on Oct. 22, 2014.

(51) Int. Cl.
*A61N 1/05* (2006.01)
*A61N 1/372* (2006.01)
*A61N 1/375* (2006.01)
*A61M 25/00* (2006.01)

(52) U.S. Cl.
CPC ....... *A61N 1/0587* (2013.01); *A61M 25/0068* (2013.01); *A61N 1/3756* (2013.01); *A61N 1/37205* (2013.01); *A61M 25/0069* (2013.01); *A61M 2025/0081* (2013.01)

(58) Field of Classification Search
CPC .............. A61N 1/0587; A61N 1/37205; A61N 1/3756; A61M 25/0068; A61M 25/0069; A61M 2025/0081; A61M 25/0053
See application file for complete search history.

(56) References Cited

U.S. PATENT DOCUMENTS

| | | | |
|---|---|---|---|
| 4,301,815 A | 11/1981 | Doring | |
| 5,078,702 A * | 1/1992 | Pomeranz | A61M 25/001 600/435 |
| 5,238,004 A | 8/1993 | Sahatjian et al. | |
| 5,772,641 A * | 6/1998 | Wilson | A61M 25/0009 604/523 |
| 5,807,399 A | 9/1998 | Laske et al. | |
| 5,908,381 A | 6/1999 | Aznoian et al. | |
| 6,181,973 B1 | 1/2001 | Ceron et al. | |
| 6,217,566 B1 * | 4/2001 | Ju | A61M 25/005 604/526 |
| 6,395,017 B1 | 5/2002 | Dwyer et al. | |
| 6,409,674 B1 | 6/2002 | Brockway et al. | |
| 6,508,803 B1 | 1/2003 | Horikawa et al. | |

(Continued)

*Primary Examiner* — Erich G Herbermann
(74) *Attorney, Agent, or Firm* — Seager, Tufte & Wickhem LLP

(57) ABSTRACT

Delivery devices, systems, and methods for delivering implantable leadless pacing devices are disclosed. An example delivery device may include a proximal section including a deflection mechanism for deflecting the proximal section, and a distal holding section extending distally of a distal end of the proximal section and defining a cavity therein for receiving an implantable leadless pacing device. The distal holding section may be structured to have portions that flex and bend while allowing the implantable device to be recaptured within the distal holding section.

20 Claims, 16 Drawing Sheets

(56) References Cited

U.S. PATENT DOCUMENTS

| | | | |
|---|---|---|---|
| 6,582,441 B1 | 6/2003 | He et al. | |
| 6,638,268 B2 | 10/2003 | Niazi | |
| 6,726,700 B1 * | 4/2004 | Levine | A61M 25/0147 606/194 |
| 6,786,918 B1 | 9/2004 | Krivoruchko et al. | |
| 7,381,216 B2 | 6/2008 | Buzzard et al. | |
| 7,499,758 B2 | 3/2009 | Cates et al. | |
| 7,608,099 B2 | 10/2009 | Johnson et al. | |
| 7,799,037 B1 | 9/2010 | He et al. | |
| 7,840,281 B2 | 11/2010 | Kveen et al. | |
| 7,993,351 B2 | 8/2011 | Worley et al. | |
| 8,010,209 B2 | 8/2011 | Jacobson | |
| 8,103,361 B2 | 1/2012 | Moser | |
| 8,185,213 B2 | 5/2012 | Kveen et al. | |
| 8,267,987 B2 | 9/2012 | Johnson et al. | |
| 8,352,028 B2 | 1/2013 | Wenger | |
| 8,364,280 B2 | 1/2013 | Marnfeldt et al. | |
| 8,377,035 B2 * | 2/2013 | Zhou | A61M 25/0053 604/524 |
| 8,382,813 B2 | 2/2013 | Shumer | |
| 8,428,750 B2 | 4/2013 | Kolberg | |
| 8,478,431 B2 | 7/2013 | Griswold et al. | |
| 8,504,156 B2 | 8/2013 | Bonner et al. | |
| 8,527,068 B2 | 9/2013 | Ostroff | |
| 8,532,790 B2 | 9/2013 | Griswold | |
| 8,548,605 B2 | 10/2013 | Ollivier | |
| 8,615,310 B2 | 12/2013 | Khairkhahan et al. | |
| 8,634,912 B2 | 1/2014 | Bornzin et al. | |
| 8,721,587 B2 | 5/2014 | Berthiaume et al. | |
| 8,727,996 B2 | 5/2014 | Allan et al. | |
| 8,758,365 B2 | 6/2014 | Bonner et al. | |
| 8,855,789 B2 | 10/2014 | Jacobson | |
| 8,903,513 B2 | 12/2014 | Ollivier | |
| 8,926,588 B2 | 1/2015 | Berthiaume et al. | |
| 8,945,145 B2 | 2/2015 | Tran et al. | |
| 8,945,146 B2 | 2/2015 | Steingisser et al. | |
| 8,948,883 B2 | 2/2015 | Eggen et al. | |
| 8,958,892 B2 | 2/2015 | Khairkhahan et al. | |
| 9,020,611 B2 | 4/2015 | Khairkhahan et al. | |
| 9,072,872 B2 | 7/2015 | Asleson et al. | |
| 9,101,281 B2 | 8/2015 | Reinert et al. | |
| 9,119,959 B2 | 9/2015 | Rys et al. | |
| 9,126,032 B2 | 9/2015 | Khairkhahan et al. | |
| 2001/0052345 A1 | 12/2001 | Niazi | |
| 2003/0078618 A1 * | 4/2003 | Fey | A61B 5/6882 607/2 |
| 2003/0216642 A1 * | 11/2003 | Pepin | A61L 29/106 600/431 |
| 2004/0019359 A1 | 1/2004 | Worley et al. | |
| 2004/0193180 A1 | 9/2004 | Buzzard et al. | |
| 2004/0230280 A1 | 11/2004 | Cates et al. | |
| 2005/0267555 A1 | 12/2005 | Marnfeldt et al. | |
| 2006/0200222 A1 | 9/2006 | Johnson et al. | |
| 2007/0088418 A1 | 4/2007 | Jacobson | |
| 2007/0191864 A1 | 8/2007 | Shumer | |
| 2007/0233218 A1 | 10/2007 | Kolberg | |
| 2008/0021532 A1 | 1/2008 | Kveen et al. | |
| 2009/0082828 A1 | 3/2009 | Ostroff | |
| 2009/0281605 A1 | 11/2009 | Marnfeldt et al. | |
| 2010/0004732 A1 | 1/2010 | Johnson et al. | |
| 2010/0198288 A1 | 8/2010 | Ostroff | |
| 2010/0274227 A1 | 10/2010 | Khairkhahan et al. | |
| 2011/0009944 A1 | 1/2011 | Moser | |
| 2011/0034939 A1 | 2/2011 | Kveen et al. | |
| 2011/0112548 A1 | 5/2011 | Fifer et al. | |
| 2011/0237967 A1 | 9/2011 | Moore et al. | |
| 2011/0238077 A1 | 9/2011 | Wenger | |
| 2011/0251660 A1 | 10/2011 | Griswold | |
| 2011/0251662 A1 | 10/2011 | Griswold et al. | |
| 2011/0270339 A1 | 11/2011 | Murray, III et al. | |
| 2011/0270340 A1 | 11/2011 | Pellegrini et al. | |
| 2011/0282423 A1 | 11/2011 | Jacobson | |
| 2011/0307043 A1 | 12/2011 | Ollivier | |
| 2012/0095539 A1 | 4/2012 | Khairkhahan et al. | |
| 2012/0109002 A1 | 5/2012 | Mothilal et al. | |
| 2012/0109079 A1 | 5/2012 | Asleson et al. | |
| 2012/0109148 A1 | 5/2012 | Bonner et al. | |
| 2012/0109149 A1 | 5/2012 | Bonner et al. | |
| 2012/0116489 A1 | 5/2012 | Khairkhahan et al. | |
| 2012/0158111 A1 | 6/2012 | Khairkhahan et al. | |
| 2012/0165827 A1 | 6/2012 | Khairkhahan et al. | |
| 2012/0172690 A1 | 7/2012 | Anderson et al. | |
| 2012/0172891 A1 | 7/2012 | Lee | |
| 2012/0172892 A1 | 7/2012 | Grubac et al. | |
| 2012/0197373 A1 | 8/2012 | Khairkhahan et al. | |
| 2012/0232565 A1 | 9/2012 | Kveen et al. | |
| 2012/0271134 A1 | 10/2012 | Allan et al. | |
| 2013/0012925 A1 | 1/2013 | Berthiaume et al. | |
| 2013/0035636 A1 | 2/2013 | Beasley et al. | |
| 2013/0035748 A1 | 2/2013 | Bonner et al. | |
| 2013/0053921 A1 | 2/2013 | Bonner et al. | |
| 2013/0079798 A1 | 3/2013 | Tran et al. | |
| 2013/0079861 A1 | 3/2013 | Reinert et al. | |
| 2013/0103047 A1 * | 4/2013 | Steingisser | A61N 1/3756 606/129 |
| 2013/0116741 A1 | 5/2013 | Bornzin et al. | |
| 2013/0123827 A1 * | 5/2013 | Kellerman | A61M 25/09 606/185 |
| 2013/0131591 A1 | 5/2013 | Berthiaume et al. | |
| 2013/0131693 A1 | 5/2013 | Berthiaume et al. | |
| 2013/0253342 A1 | 9/2013 | Griswold et al. | |
| 2013/0253343 A1 | 9/2013 | Naldhauser et al. | |
| 2013/0253344 A1 | 9/2013 | Griswold et al. | |
| 2013/0253345 A1 | 9/2013 | Griswold et al. | |
| 2013/0253346 A1 | 9/2013 | Griswold et al. | |
| 2013/0253347 A1 | 9/2013 | Griswold et al. | |
| 2014/0018818 A1 | 1/2014 | Somogyi et al. | |
| 2014/0031836 A1 | 1/2014 | Ollivier | |
| 2014/0058494 A1 | 2/2014 | Ostroff et al. | |
| 2014/0074114 A1 | 3/2014 | Khairkhahan et al. | |
| 2014/0148815 A1 | 5/2014 | Wenzel et al. | |
| 2014/0180306 A1 | 6/2014 | Grubac et al. | |
| 2014/0249543 A1 | 9/2014 | Berthiaume et al. | |
| 2014/0257324 A1 | 9/2014 | Fain | |
| 2014/0303704 A1 | 10/2014 | Suwito et al. | |
| 2014/0324145 A1 | 10/2014 | Eggen et al. | |
| 2014/0378991 A1 | 12/2014 | Ollivier | |
| 2015/0039069 A1 | 2/2015 | Rys et al. | |
| 2015/0039070 A1 | 2/2015 | Kuhn et al. | |
| 2015/0039071 A1 | 2/2015 | Grubac et al. | |
| 2015/0045868 A1 | 2/2015 | Bonner et al. | |
| 2015/0051613 A1 | 2/2015 | Schmidt et al. | |
| 2015/0051614 A1 | 2/2015 | Schmidt et al. | |
| 2015/0051615 A1 | 2/2015 | Schmidt et al. | |
| 2015/0051682 A1 | 2/2015 | Schmidt et al. | |
| 2015/0094668 A1 | 4/2015 | Wood et al. | |
| 2015/0094735 A1 | 4/2015 | Ward et al. | |
| 2015/0112361 A1 | 4/2015 | Khairkhahan et al. | |
| 2015/0148815 A1 | 5/2015 | Steingisser et al. | |
| 2015/0151117 A1 | 6/2015 | Eggen et al. | |
| 2015/0273207 A1 | 10/2015 | Tran et al. | |
| 2015/0273212 A1 | 10/2015 | Berthiaume et al. | |
| 2015/0297899 A1 | 10/2015 | Ostroff | |
| 2015/0335884 A1 | 11/2015 | Khairkhahan et al. | |
| 2015/0352351 A1 | 12/2015 | Muessig et al. | |
| 2015/0352353 A1 | 12/2015 | Rys et al. | |
| 2016/0000563 A1 | 1/2016 | Asleson et al. | |

* cited by examiner

DELIVERY DEVICES AND METHODS FOR LEADLESS CARDIAC DEVICES

CROSS-REFERENCE TO RELATED APPLICATIONS

This application claims priority under 35 U.S.C. § 119 to U.S. Provisional Application Ser. No. 62/067,074, filed Oct. 22, 2014, the entirety of which is incorporated herein by reference.

TECHNICAL FIELD

The present disclosure pertains to medical devices, and methods for manufacturing and/or using medical devices. More particularly, the present disclosure pertains to leadless cardiac devices and methods, such as leadless pacing devices and methods, and delivery devices and methods for such leadless devices.

BACKGROUND

A wide variety of medical devices have been developed for medical use, for example, cardiac use. Some of these devices include catheters, leads, pacemakers, and the like, and delivery devices and/or systems used for delivering such devices. These devices are manufactured by any one of a variety of different manufacturing methods and may be used according to any one of a variety of methods. Of the known medical devices, delivery systems, and methods, each has certain advantages and disadvantages. There is an ongoing need to provide alternative medical devices and delivery devices as well as alternative methods for manufacturing and using medical devices and delivery devices.

BRIEF SUMMARY

This disclosure provides design, material, manufacturing method, and use alternatives for medical devices, including delivery devices.

In a first example, a delivery device for delivering an implantable leadless pacing device may comprise a proximal section, a distal holding section extending distally of a distal end of the proximal section, the distal holding section defining a cavity therein for receiving an implantable leadless pacing device, and wherein the distal holding section comprises a reinforcing element covered by a polymeric body, such as a reinforcing element embedded within a polymeric body.

Alternatively or additionally to any of the examples above, in another example, the reinforcing element may comprise a nitinol cage.

Alternatively or additionally to any of the examples above, in another example, the nitinol cage may comprise a distal band, a proximal band, and a plurality of struts extending between the distal band and the proximal band.

Alternatively or additionally to any of the examples above, in another example, the reinforcing element may comprise a helically wound coil embedded within the polymeric body.

Alternatively or additionally to any of the examples above, in another example, the helically wound coil may extend along a length of the distal holding section, the length extending from a point adjacent a distal tip of the distal holding section to a point distal to a proximal end of the distal holding section.

Alternatively or additionally to any of the examples above, in another example, the distal holding section may comprise a first polymer having a first durometer along the length of the helically wound coil and a second polymer having a second durometer extending from a proximal end of the helically wound coil to the proximal end of the distal holding section.

Alternatively or additionally to any of the examples above, in another example, the first durometer may be less than the second durometer.

Alternatively or additionally to any of the examples above, in another example, the helically wound coil may extend from a distal end region of the distal holding section to a proximal end region of the distal holding section.

Alternatively or additionally to any of the examples above, in another example, the helically wound coil may comprise a proximal section having a first pitch and a distal section having a second pitch.

Alternatively or additionally to any of the examples above, in another example, the first pitch may be less than the second pitch.

Alternatively or additionally to any of the examples above, in another example, the reinforcing element may comprise a braided reinforcing element.

Alternatively or additionally to any of the examples above, in another example, the braided reinforcing element may comprise a proximal section having a first pitch and a distal section having a second pitch different from the first pitch.

Alternatively or additionally to any of the examples above, in another example, the device may further comprise one or more apertures extending through a wall of the distal holding section.

Alternatively or additionally to any of the examples above, in another example, a density of the one or more apertures may increase from a proximal end to or toward a distal tip of the distal holding section.

Alternatively or additionally to any of the examples above, in another example, the one or more apertures may comprise a spiral cut extending along a length of the distal holding section.

Alternatively or additionally to any of the examples above, in another example, the distal holding section may comprise a predefined curved portion along a length thereof.

Alternatively or additionally to any of the examples above, in another example, the distal holding section may comprise a shape memory polymer.

Alternatively or additionally to any of the examples above, in another example, a delivery device for delivering an implantable leadless pacing device may comprise a proximal section, a distal holding section extending distally of a distal end of the proximal section, the distal holding section defining a cavity therein for receiving an implantable leadless pacing device, and wherein the distal holding section comprises a reinforcing element covered by a polymeric body, such as a reinforcing element embedded within a polymeric body.

Alternatively or additionally to any of the examples above, in another example, the reinforcing element may comprise a nitinol cage.

Alternatively or additionally to any of the examples above, in another example, the nitinol cage may comprise a distal band, a proximal band, and a plurality of struts extending between the distal band and the proximal band.

Alternatively or additionally to any of the examples above, in another example, the reinforcing element may comprise a helically wound coil embedded within the polymeric body.

Alternatively or additionally to any of the examples above, in another example, the helically wound coil may extend along a length of the distal holding section, the length extending from a point adjacent a distal tip of the distal holding section to a point distal to a proximal end of the distal holding section.

Alternatively or additionally to any of the examples above, in another example, the distal holding section may comprise a first polymer having a first durometer along the length of the helically wound coil and a second polymer having a second durometer extending from a proximal end of the helically wound coil to the proximal end of the distal holding section.

Alternatively or additionally to any of the examples above, in another example, the first durometer may be less than the second durometer.

Alternatively or additionally to any of the examples above, in another example, the helically wound coil may extend from a distal end of the distal holding section to or toward a proximal holding section.

Alternatively or additionally to any of the examples above, in another example, the helically wound coil may comprise a proximal section having a first pitch and a distal section having a second pitch.

Alternatively or additionally to any of the examples above, in another example, the helically wound coil protrudes from an inner surface of the distal holding section.

Alternatively or additionally to any of the examples above, in another example, the reinforcing element may comprise a braided reinforcing element embedded within the polymeric body.

Alternatively or additionally to any of the examples above, in another example, a delivery device for delivering an implantable leadless pacing device may comprise a proximal section, a distal holding section extending distally of a distal end of the proximal section, the distal holding section defining a cavity therein for receiving an implantable leadless pacing device, and wherein the distal holding section comprises a polymeric body and one or more apertures extending through a wall of the polymeric body.

Alternatively or additionally to any of the examples above, in another example, a density of the one or more apertures may increase from a proximal end to or toward a distal tip of the distal holding section.

Alternatively or additionally to any of the examples above, in another example, the one or more apertures may comprise a spiral cut extending along a length of the distal holding section.

Alternatively or additionally to any of the examples above, in another example, a pitch of the spiral cut may vary over the length of the distal holding section.

Alternatively or additionally to any of the examples above, in another example, the device may further comprise an ionically conductive coating disposed over an outer surface of the distal holding section and covering the one or more apertures.

Alternatively or additionally to any of the examples above, in another example, the device may further comprise a reinforcing element disposed adjacent a distal tip of the distal holding section.

Alternatively or additionally to any of the examples above, in another example, the reinforcing element may have a "C" shape configured to allow a distal end region of the distal holding section to expand.

Alternatively or additionally to any of the examples above, in another example, a delivery device for delivering an implantable leadless pacing device may comprise a proximal section, a distal holding section extending distally of a distal end of the proximal section, the distal holding section defining a cavity therein for receiving an implantable leadless pacing device, and wherein the distal holding section comprises a predefined curved portion along a length thereof.

Alternatively or additionally to any of the examples above, in another example, the distal holding section may straighten to extend generally parallel to a longitudinal axis of the proximal section when an implantable leadless pacing device is disposed within the cavity.

Alternatively or additionally to any of the examples above, in another example, the distal holding section may comprise a shape memory polymer.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

The disclosure may be more completely understood in consideration of the following detailed description in connection with the accompanying drawings, in which.

Figure 1:
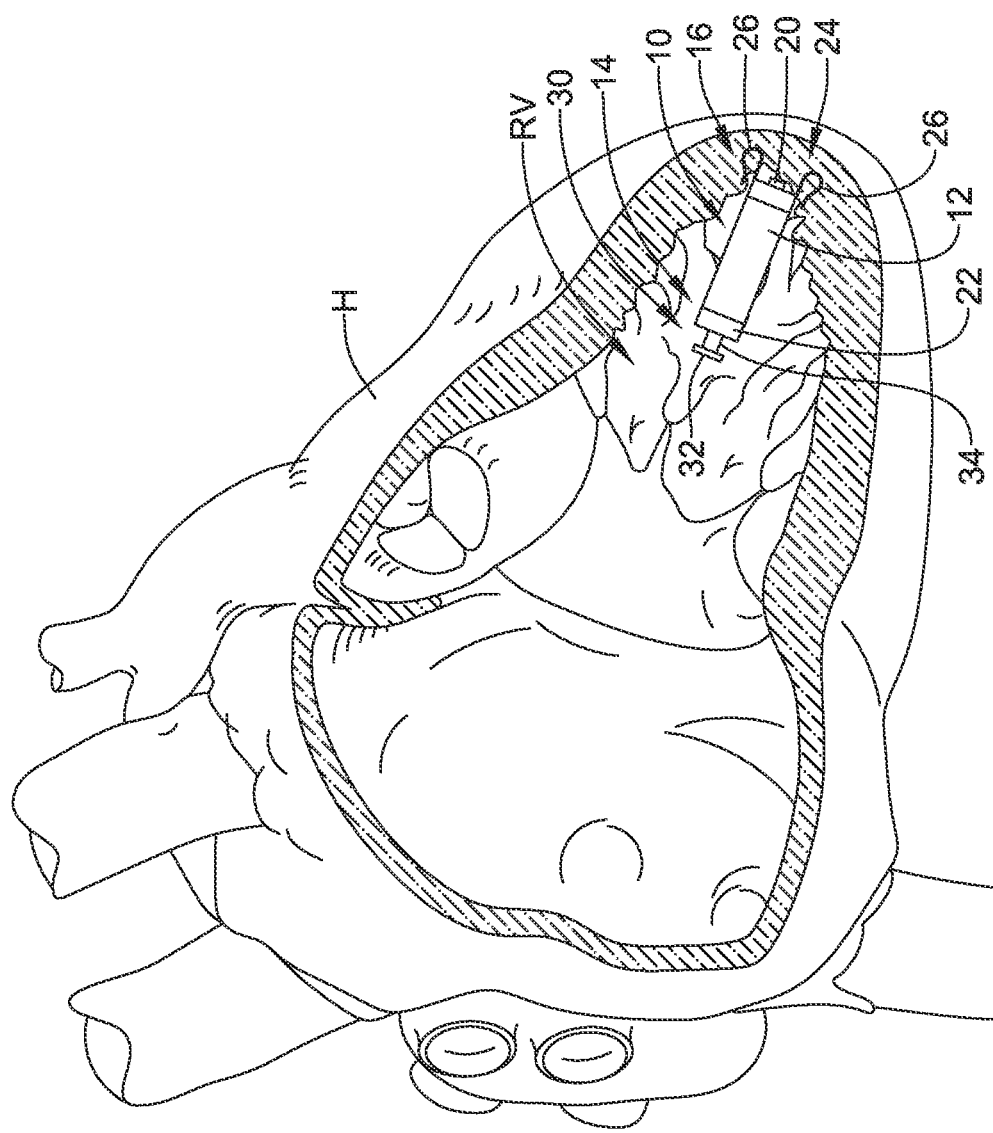
FIG. 1 is a plan view of an example leadless pacing device implanted within a heart.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

Cardiac pacemakers provide electrical stimulation to heart tissue to cause the heart to contract and thus pump blood through the vascular system. Conventional pacemakers typically include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules typically fixed to an intracardiac implant site in a cardiac chamber. The small capsule typically includes bipolar pacing/sensing electrodes, a power source (e.g. a battery), and associated electrical circuitry for controlling the pacing/sensing electrodes, and thus provide electrical stimulation to heart tissue and/or sense a physiological condition. It can be readily appreciated that the implantation of a leadless pacing device within a beating heart could become dislodged as the heart functions. Accordingly, it may be desirable for a leadless pacing device to include one or more anchoring mechanism or member to help securing the pacing device to the heart.

FIG. 1 illustrates an example implantable leadless cardiac pacing device 10 (e.g., a leadless pacemaker) implanted in a chamber of a heart H, such as the right ventricle RV. The implantable device 10 may include a shell or housing 12 having a proximal end 14 and a distal end 16. The implantable device 10 may include a first electrode 20 positioned adjacent to the distal end 16 of the housing 12 and a second electrode 22 positioned adjacent to the proximal end 14 of the housing 12. For example, housing 12 may include a conductive material and may be insulated along a portion of its length. A section along proximal end 14 may be free of insulation so as to define second electrode 22. The electrodes 20, 22 may be sensing and/or pacing electrodes to provide electro-therapy and/or sensing capabilities. The first electrode 20 may be capable of being positioned against or otherwise contact the cardiac tissue of the heart H while the second electrode 22 may be spaced away from the first electrode 20, and thus spaced away from the cardiac tissue.

The implantable device 10 may include a pulse generator (e.g., electrical circuitry) and a power source (e.g., a battery) within the housing 12 to provide electrical signals to the electrodes 20, 22 and thus control the pacing/sensing electrodes 20, 22. Electrical communication between the pulse generator and the electrodes 20, 22 may provide electrical stimulation to heart tissue and/or sense a physiological condition.

The implantable device 10 may include a fixation mechanism 24 proximate the distal end 16 of the housing 12 configured to attach the implantable device 10 to a tissue wall of the heart H, or otherwise anchor the implantable device 10 to the anatomy of the patient. As shown in FIG. 1, in some instances, the fixation mechanism 24 may include one or more, or a plurality of hooks 26 anchored into the cardiac tissue of the heart H to attach the implantable device 10 to a tissue wall. In other instances, the fixation mechanism 24 may include one or more, or a plurality of passive tines, configured to entangle with trabeculae within the chamber of the heart H and/or a helical fixation anchor configured to be screwed into a tissue wall to anchor the implantable device 10 to the heart H.

The implantable device 10 may include a docking member 30 proximate the proximal end 14 of the housing 12 configured to facilitate delivery and/or retrieval of the implantable device 10. For example, the docking member 30 may extend from the proximal end 14 of the housing 12 along a longitudinal axis of the housing 12. The docking member 30 may include a head portion 32 and a neck portion 34 extending between the housing 12 and the head portion 32. The head portion 32 may be an enlarged portion relative to the neck portion 34. For example, the head portion 32 may have a radial dimension from the longitudinal axis of the implantable device 10 which is greater than a radial dimension of the neck portion from the longitudinal axis of the implantable device 10. The docking member 30 may be configured to facilitate delivery of the implantable device 10 to the intracardiac site and/or retrieval of the implantable device 10 from the intracardiac site. Other docking members 30 are contemplated.

One aspect of the current disclosure relates to the delivery device and/or system used, for example, to deliver device 10 to a suitable location within the anatomy (e.g., the heart). As may be appreciated, the delivery device may need to be navigated through relatively tortuous anatomy to deliver the device 10 to a suitable location. For instance, in some embodiments, the delivery device may be advanced through the vasculature to a target region. In some example cases the device may be advanced through a femoral vein, into the inferior vena cava, into the right atrium, through the tricuspid valve, and into the right ventricle. The target region for the delivery of the device 10 may be a portion of the right ventricle, for example, a portion of the right ventricle near the apex of the heart. The target region may also include other regions of the heart (e.g., right atrium, left atrium, or left ventricle), blood vessels, or other suitable targets. It may be desirable to provide the delivery system with certain features that may allow for easier or better control for navigation or delivery purposes. It may also be desirable to provide the delivery system with certain features that may facilitate retrieval of the implantable device 10.

Figure 2:
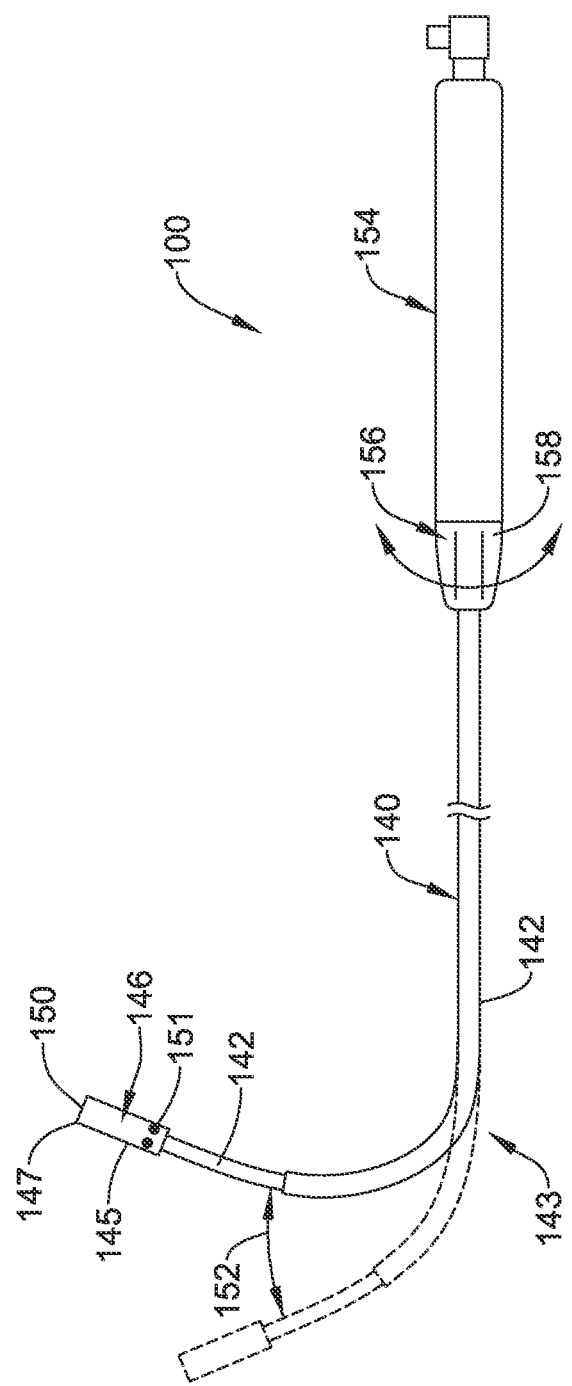
FIG. 2 is a side view of an example delivery device for an implantable leadless cardiac pacing device.
Figure 3:
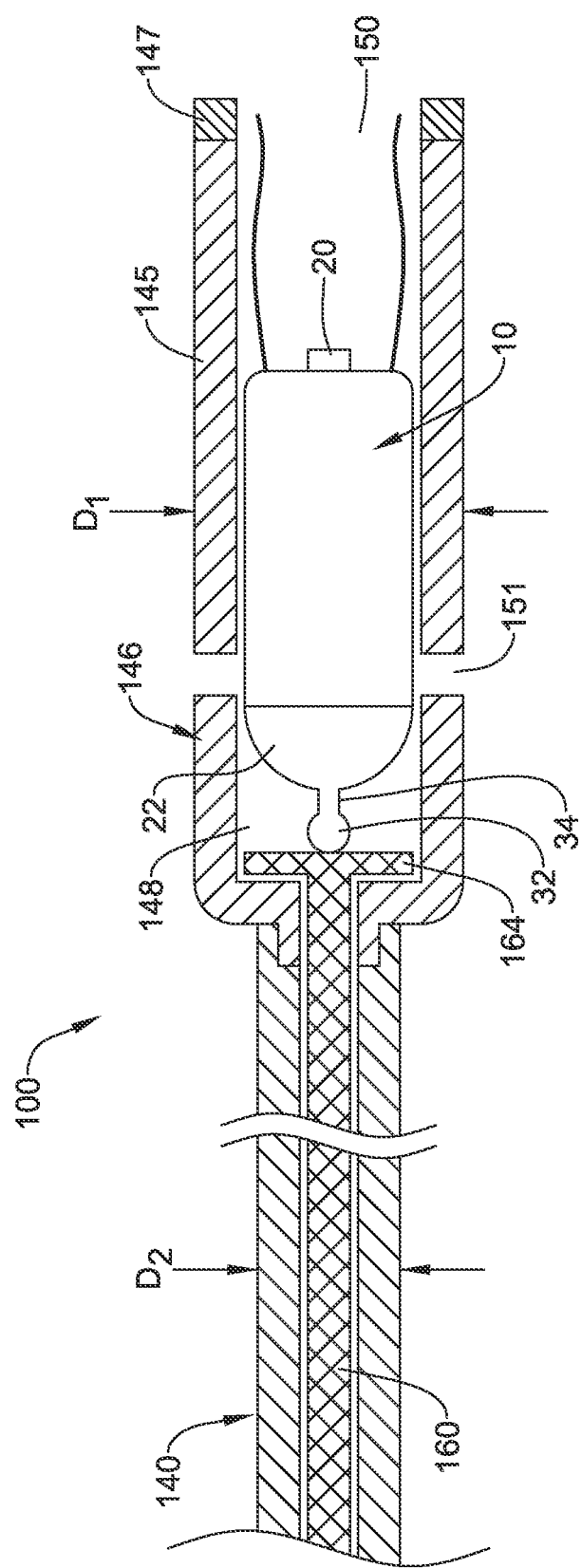
FIG. 3 is a partial cross-sectional side view of the distal portion of the delivery device of FIG. 2, showing the implantable leadless cardiac pacing device disposed therein.

FIGS. 2 and 3 illustrate an example embodiment of a delivery device 100, such as a catheter, that may be used to deliver the device 10. The delivery device 100 may include a proximal section 140, such as a proximal shaft, and a distal section and/or holding section 146, attached to the distal end of the proximal section 140. The delivery device 100 may also include a proximal hub portion 154 attached to the proximal end of the proximal section 140. In some embodiments, the proximal section 140 may include at least a section thereof that has an outer diameter D2 that is less than the outer diameter D1 of at least a portion of the holding section 146. (See e.g. FIG. 3).

The distal holding section 146 may be configured to receive the implantable device 10 therein. For example, referring to both FIGS. 2 and 3, the holding section 146 may define a cavity 148 for slidably receiving the implantable device 10, and may include a distal opening 150 for slidable insertion and/or extraction of the implantable device 10 into and/or out of the cavity 148. Other suitable distal holding sections that are able to receive the implantable device 10 therein may also be used. Such alternative holding sections may be applied to all other embodiments shown and/or discussed herein, and others, as appropriate.

The distal holding section 146 may include a body portion 145 and a distal tip portion 147 that may, for example, be configured to be atraumatic to anatomy, such as a bumper tip. For example, as the catheter is navigated through the anatomy, the distal tip may come into contact with anatomy. Additionally, when the catheter is used to deliver the device, the tip 147 of the delivery device 100 will likely come into contact with tissue adjacent the target site (e.g. cardiac tissue of the heart). A hard distal tip formed of the material of the elongate proximal section 140 may injure a vessel wall or cardiac tissue. As such, it may be desirable to provide the delivery device 100 with a softer distal tip that can be introduced into the anatomy and come into contact with anatomy adjacent the target site without causing unnecessary trauma.

For example, the distal tip 147 may be made of a material that is softer than the body portion 145 of the distal holding section. In some cases, the distal tip 147 may include a material that has a durometer that is less than the durometer of the material of the body portion 145. In some particular embodiments, the durometer of the material used in the distal tip 147 may be in the range of about 5 D to about 70 D, or for example, in the range of about 25 D to about 65 D. Additionally, the distal tip 147 may include a shape or structure that may make it less traumatic to tissue. For example, the distal tip 147 may have a distal surface, such as a tissue contacting surface, that is rounded or includes a curvature configured to be more atraumatic to tissue.

In some embodiments, all or a portion of the distal holding section 146 may include an inner surface that may be configured to resist getting caught on the fixation mechanism 24, such as the one or more, or a plurality of hooks 26 on the device 10. For example, the distal holding section 146 may include an inner layer or coating of harder or more lubricious material that resists force applied by the fixation mechanism 24 onto the inner surface of the distal holding section 146. For example, the distal holding section 146 may include a multi-layered structure, and an inner layer may be made of a material that is harder than an outer layer.

The distal holding section 146 may also define one or more conductive pathways 151 that are spaced proximally from the distal opening 150 in the distal end of the distal holding section. For example, the conductive pathways 151 may include one or more openings through the wall of the distal holding section 146 that allow for fluid communication there through of a conductive fluid, such as blood. Such a conductive pathway may allow for conductive communication between electrodes 20, 22 on the device 10 through the distal opening 150 and the pathway openings 151 respectively, while the device is housed within the cavity 148. Such communication may allow the device 10 to be tested prior to being released or delivered out of the cavity 148. Other conductive pathways are also contemplated. For example, the one or more conductive pathways may include one or more sections defined in the wall of the distal holding section 146 that comprises a conductive material, such as conductive metals, polymers, and the like. In at least some embodiments, the distal holding section 146 may be free of the conductive pathways 151.

A push member 160 may be disposed (e.g., slidably disposed) within a lumen of the delivery device 100. The push member 160 may be engaged by a user near the proximal end of the delivery device 100, and extend through a lumen in the delivery device 100, through the proximal section 140 and into the distal holding section 146. A distal portion 164 of the push member 160 may be capable of engaging the device 10, and the push member 160 may be used to "push" device 10 out from distal holding section 146 so as to deploy and anchor device 10 within a target region (e.g., a region of the heart such as the right ventricle).

In order to more specifically place or steer delivery device 100 to a position adjacent to the intended target, delivery device 100 may be configured to be deflectable or articulable or steerable. Referring to FIG. 2, for example, the proximal section 140 may include one or more articulation or deflection mechanism(s) that may allow for the catheter 100, or portions thereof, to be deflected, articulated, steered and/or controlled in a desired manner. For example, the proximal section 140 may include a shaft, such as a tubular shaft member 142 that includes at least a portion thereof that can be selectively bent and/or deflected in a desired or predetermined direction. This may, for example, allow a user to orient the delivery device 100 such that the holding section 146 is in a desirable position or orientation for navigation or delivery of the device 10 to a target location. As shown in FIG. 2, the shaft member 142 may be deflected, for example, along deflection region 143 from a first example position indicated in phantom lines, to a second example position indicated in solid lines along a deflection path 152.

A wide variety of deflection mechanisms may be used. In some example embodiments, deflection may be effected by one or more actuation members, such as pull wire(s) extending between a distal portion of the catheter shaft member 142 and an actuation mechanism 156 near the proximal end of the shaft member 142. As such, the one or more pull wires may extend both proximally and distally of the desired deflection or bending region or point. This allows a user to actuate (e.g., "pull") one or more of the pull wires to apply a compression and/or deflection force to at least a portion of the shaft 142 and thereby deflect or bend the shaft member 142 in a desired manner. In addition, in some cases the one or more wires may be stiff enough so that they can also be used to provide a pushing and/or tensioning force on the shaft member 142, for example, to "push" or "straighten" the shaft into a desired position or orientation.

In some embodiments, the actuation member takes the form of a continuous wire that is looped through or otherwise coupled to a distal end of the shaft member 142 so as to define a pair of wire sections. Other embodiments are contemplated, however, including embodiments where the actuation member includes one or a plurality of individual wires that are attached, for example, to the distal end of the shaft member 142.

The actuation mechanism 156 may include a desired mechanism that may allow for applying tension (i.e. pulling force), or compression (i.e. pushing force), or both, on the actuation member(s). In some embodiments, the actuation mechanism 156 may include an external rotatable member 158 connected to and rotatable about the longitudinal axis of the hub 154. The rotatable member 158 may threadingly engage an internal member that is attached to the proximal end of the actuation member(s) or pull wires. When the external rotatable member 158 is rotated in a first rotational direction, the internal member translates in a first longitudinal direction, thereby applying tension to the pull wires, which applies compression force to the shaft, so as to deflect the shaft member 142 from an initial position to a deflected position. When the external rotatable member 158 is rotated in a second rotational direction, the internal member translates in a second longitudinal direction, thereby releasing the tension on the pull wires, and allowing the shaft member 142 to relax back toward the initial position. Additionally, in some cases, as mentioned above, where the one or more wires may be sufficiently rigid, rotation of the rotatable member 158 in the second rotational direction such that the internal member translates in a second longitudinal direction may apply compression to the wires, such that the wires may apply tension to the shaft member 142 and "push" the shaft member 142 back toward an initial position, and possibly into additional positions beyond the initial position.

The one or more articulation and/or deflection mechanism(s) may also entail the shaft member 142 including structure and/or material that may provide for the desired degree and/or location of the deflection when the compressive or tensile forces are applied. For example, the shaft member 142 may include one or more sections that include structure and/or material configured to allow the shaft to bend and/or deflect in a certain way when a certain predetermined compressive and/or tensile force is applied. For example, the shaft may include one or more sections that are more flexible than other sections, thereby defining a bending or articulating region or location. Some such regions may include a number of varying or changing flexibility characteristics that may define certain bending shapes when predetermined forces are applied. Such characteristics may be achieved through the selection of materials or structure for different sections of the shaft member 142.

In other embodiments, other articulation and/or deflection mechanism(s) are contemplated. For example, all or a portion of the delivery device 100, such as the proximal section 140, such as shaft member 142, may be made of a shape memory material, such as a shape memory polymer and/or a shape memory metal. Such materials, when stimulated by an actuation mechanism, such as a change in temperature or the application of an electrical current, may change or move from a first shape to a second shape. As such, these materials and mechanisms may be used to deflect or bend the shaft member 142 in a desired manner. Other suitable deflection mechanism(s) that are able to deflect the delivery device 100 may also be used. For example, at least a portion of the shaft member 142, or other component of the delivery device 100, may include an electroactive polymer (EAP) which may be electrically activated to selectively deflect the delivery device 100. Such alternative mechanisms may be applied to all other embodiments shown and/or discussed herein, and others, as appropriate.

Furthermore, the shaft member 142 may include one or more predefined or fixed curved portion(s) along the length thereof. In some cases, such curved sections may be configured to fit with particular anatomies or be configured for better navigation or delivery of the device 10. Additionally, or alternatively, some such curved sections may be configured to allow the shaft member 142 to be predisposed to be bent and/or deflected in a certain direction or configuration when compression and/or tension forces are applied thereto.

Figure 4:
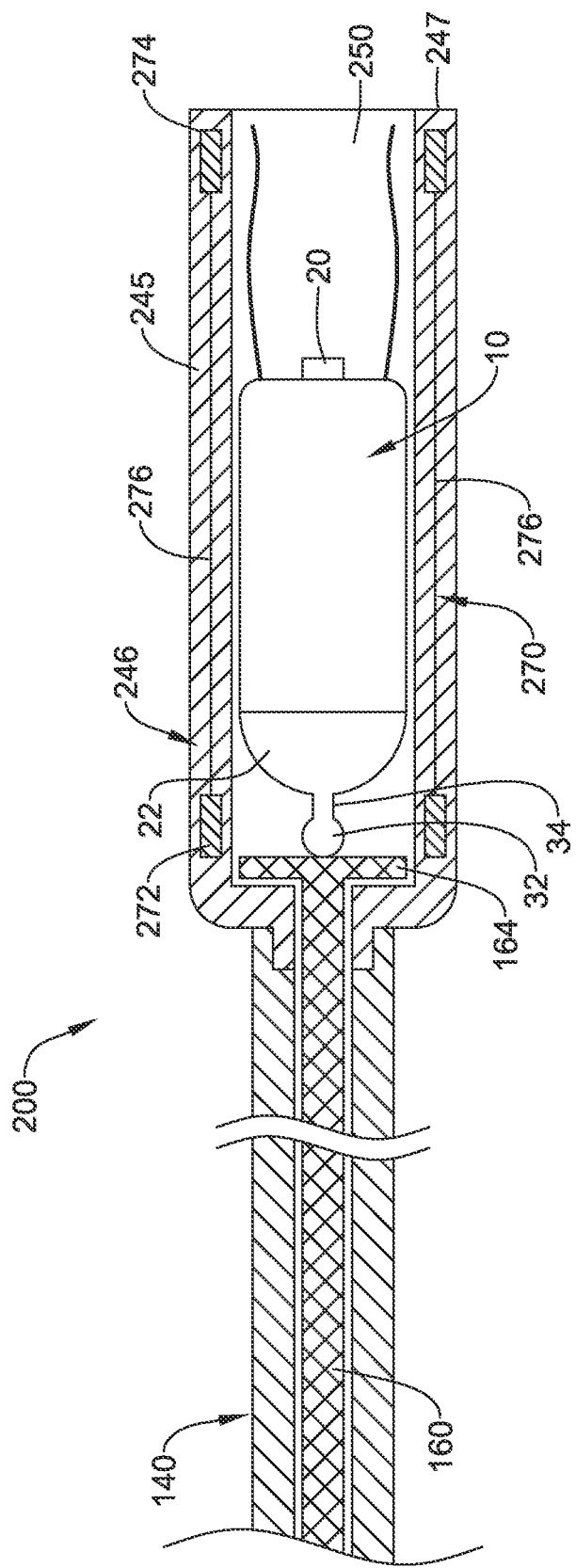
FIG. 4 is a partial cross-sectional side view of the distal portion of another illustrative delivery device, showing the implantable leadless cardiac pacing device disposed therein.

FIG. 4 illustrates a partial cross-sectional side view of the distal portion of a delivery device 200, such as a catheter, which is similar in many respects to that of the delivery device 100 shown in FIG. 2, with similar structures numbered the same. The delivery device 200 may include a proximal section 140, such as a proximal shaft, and a distal section and/or holding section 246, attached to the distal end of the proximal section 140. The distal holding section 246 may be configured to receive the implantable device 10 therein. For example, the holding section 246 may define a cavity 248 for slidably receiving the implantable device 10, and may include a distal opening 250 for slidable insertion and/or extraction of the implantable device 10 into and/or out of the cavity 248. Other suitable distal holding sections that are able to receive the implantable device 10 therein may also be used. Such alternative holding sections may be applied to all other embodiments shown and/or discussed herein, and others, as appropriate.

The distal holding section 246 may include a body portion 245 and a distal tip portion 247 that may, for example, be configured to be atraumatic to anatomy, such as a bumper tip. In some instances, the distal tip 247 may be made of a material that is softer than the body portion 245 of the distal holding section 246, although this is not required. In some cases, the distal tip 247 may include a material that has a durometer that is less than the durometer of the material of the body portion 245. In some particular embodiments, the durometer of the material used in the distal tip 247 may be in the range of about 5 D to about 70 D, or for example, in the range of about 25 D to about 65 D. Additionally, the distal tip 247 may include a shape or structure that may make it less traumatic to tissue. For example, the distal tip 247 may have a distal surface, such as a tissue contacting surface, that is rounded or includes a curvature configured to be more atraumatic to tissue.

In some embodiments, all or a portion of the distal holding section 246 may include an inner surface that may be configured to resist getting caught on the fixation mechanism 24, such as the one or more, or a plurality of hooks 26 on the device 10. For example, the distal holding section 246 may include an inner layer or coating of harder or more lubricious material that resists force applied by the fixation mechanism 24 onto the inner surface of the distal holding section 246. For example, the distal holding section 246 may include a multi-layered structure, and an inner layer may be made of a material that is harder than an outer layer.

In some instances, it may be desirable for the distal holding section 246 to be flexible and bendable. This may allow the distal holding section 246 to be more easily aligned with the implantable device 10 in the event it needs to be recaptured within the distal holding section 246. However, it may be necessary for the distal holding section 246 to have some rigidity to allow the implantable device 10 to be drawn back into the distal holding section 246 if the device 10 needs to be relocated or otherwise moved. For example, it may be desirable for the distal holding section 246 to have some structure to prevent the distal holding section 246 from collapsing on itself, which may hinder and/or prevent recapturing the device 10. It is contemplated that the body portion 245 may be formed from a flexible material. In some instances, the body portion 245 may be a polymeric body formed from a material such as, but not limited to, silicone rubber, polyurethane (PU), or poly (ethylene glycol) (PEG). These are just examples. The polymeric body 245 may have a durometer in the range of about 20 D to about 50 D, about 30 D to about 40 D or about 35 D, for example.

The distal holding section 246 may further include a reinforcing element 270 covered by the polymeric body 245, such as embedded within the polymeric body 245. The reinforcing element 270 may be configured to provide a stable structure to the distal holding section 246 while still allowing the distal holding section 246 to flex and bend to facilitate retrieval of the device 10. In some instances, the reinforcing element 270 may include a metal or polymeric cage including a proximal band 272 positioned adjacent to a proximal end of the distal holding section 246 and/or a distal band 274 positioned adjacent to the distal tip 347. The proximal band 272 and/or the distal band 274 may be connected by one or more wires or struts 276. In some instances, the reinforcing element 270 may be formed from nitinol. This is just an example. In some embodiments, the reinforcing element 270 may include radiopaque properties to facilitate delivery and/or retrieval of the implantable device 10.

It is contemplated that the reinforcing element 270 may include one or more bands in addition to the proximal and/or distal bands 272, 274. It is further contemplated that the reinforcing element 270 may include only one of the proximal or distal bands 272, 274. In some instances, the proximal and/or distal bands 272, 274 may be circular or generally form a complete ring. In other instances, the proximal and/or distal bands 272, 274 may not form a complete ring. For example, the proximal and/or distal bands 272, 274 may have a "C" shape. It is further contemplated that the proximal and/or distal bands 272,274 may have any cross-sectional shape desired, such as, but not limited to, square, round, rectangular, pill-shaped, oval, polygonal, diamond, etc. The proximal band 272 and the distal band 274 may have the same shape or different shapes, as desired. The proximal and distal bands 272, 274 may be connected by connectors, such as a plurality of wires or struts 276 extending between the proximal band 272 and the distal band 274. There may be one, two, three, four, or more struts 276 connecting the proximal band 272 and the distal band 274, as desired, and may be symmetrically or asymmetrically circumferentially arranged around the distal holding section 246. The struts 276 may have any cross-sectional shape desired, such as, but not limited to, circular, square, rectangular, oval polygonal, etc.

While the reinforcing element 270 is described as embedded within the polymeric body 245, it is contemplated that the distal holding section 246 may be formed in other manners. For example, a polymeric jacket may be disposed over the inner and/or outer surface of the reinforcing element 270. It is contemplated that a polymeric material may be extruded or heat shrunk over the reinforcing element 270. In some instances, the distal holding section 246 may be injection molded with the reinforcing element 270. These are just examples.

Figure 5:
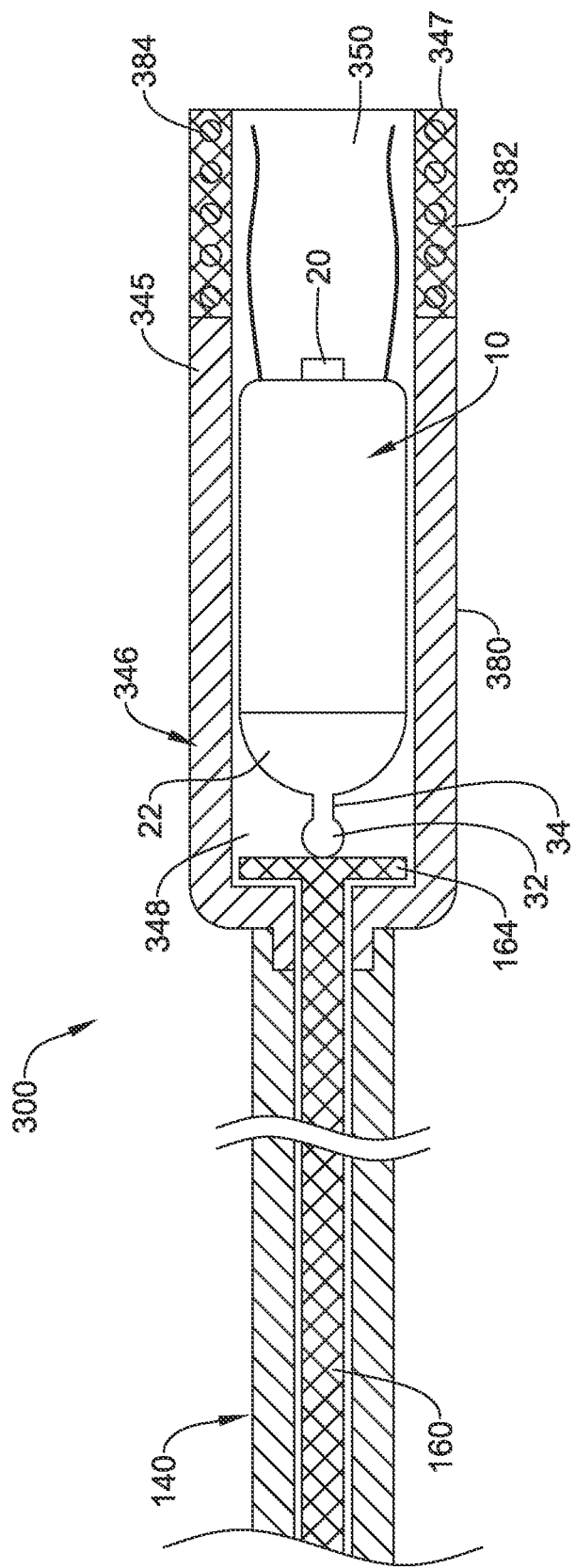
FIG. 5 is a partial cross-sectional side view of the distal portion of another illustrative delivery device, showing the implantable leadless cardiac pacing device disposed therein.

FIG. 5 illustrates a partial cross-sectional side view of the distal portion of another illustrative delivery device 300, such as a catheter, which is similar in many respects to that of the delivery device 100 shown in FIG. 2, with similar structures numbered the same. The delivery device 300 may include a proximal section 140, such as a proximal shaft, and a distal section and/or holding section 346, attached to the distal end of the proximal section 140. The distal holding section 346 may be configured to receive the implantable device 10 therein. For example, the holding section 346 may define a cavity 348 for slidably receiving the implantable device 10, and may include a distal opening 350 for slidable insertion and/or extraction of the implantable device 10 into and/or out of the cavity 348. The distal holding section 346, or portions thereof, may be configured to have portions that flex and bend while allowing the implantable device 10 to be recaptured within the distal holding section 346. Other suitable distal holding sections that are able to receive the implantable device 10 therein may also be used. Such alternative holding sections may be applied to all other embodiments shown and/or discussed herein, and others, as appropriate.

The distal holding section 346 may include a body portion 345 and a distal tip portion 347 that may be, for example, configured to be atraumatic to anatomy, such as a bumper tip. In some instances, the distal tip 347 may be made of a material that is softer than the body portion 345 of the distal holding section, although this is not required. In some cases, the distal tip 347 may include a material that has a durometer that is less than the durometer of the material of the body portion 345. Additionally, the distal tip 347 may include a shape or structure that may make it less traumatic to tissue. For example, the distal tip 347 may have a distal surface, such as a tissue contacting surface, that is that is rounded or includes a curvature configured to be more atraumatic to tissue.

In some embodiments, all or a portion of the distal holding section 346 may include an inner surface that may be configured to resist getting caught on the fixation mechanism 24, such as the one or more, or a plurality of hooks 26 on the device 10. For example, the distal holding section 346 may include an inner layer or coating of harder or more lubricious material that resists force applied by the fixation mechanism 24 onto the inner surface of the distal holding section 346. For example, the distal holding section 346 may include a multi-layered structure, and an inner layer may be made of a material that is harder than an outer layer.

The distal holding section 346 may have a proximal section 380 formed from a first material having a first durometer and a distal section 382 formed from a second material having a second durometer. In some instances, the first durometer may be greater than the second durometer. For example, the first durometer may be in the range of about 60 D to about 80 D, about 65 D to about 75 D or about 70 D. The second durometer may be in the range of about 20 D to about 50 D, about 30 D to about 40 D or about 35 D, for example. For example, the proximal section 380 may be formed from a 72 D polyether block amide and the distal section 382 may be formed from a 35 D polyether block amide. This is just an example. In some instances, the distal section 382 may include a reinforcing element, such as an embedded coil 384. The coil 384 may extend over a length extending proximally from a point adjacent the distal tip 347. It is contemplated that the coil 384 may extend over any length of the distal holding section 346 desired. The reinforcing element 384 may be configured to provide a stable structure to the distal section 382 while still allowing the distal section 382 to flex and bend to facilitate retrieval of the device 10. In some embodiments, the reinforcing element or coil 384 may extend from an inner surface of the distal holding section 346. This may create a helical or threaded path to engage a mating threaded region (not explicitly shown) on the implantable device 10. In some instances, the reinforcing element or coil 384 may be formed from stainless steel. This is just an example. In some embodiments, the reinforcing element or coil 384 may include radiopaque properties to facilitate delivery and/or retrieval of the implantable device 10.

As can be appreciated, the spacing of adjacent windings (pitch), the size, and/or shape of the coil 384 may be varied to achieve the desired characteristics. For example, a coil having a larger pitch (greater distance between adjacent windings) may be more flexible than a similarly sized and shaped coil having a smaller pitch. The filament or strut forming the reinforcing element or coil 384 may have any cross-sectional shape desired, such as, but not limited to, circular, square, rectangular, ovoid, polygonal, etc. While the reinforcing element 384 is described as embedded within the distal section 382, it is contemplated that the distal holding section 346 may be formed in other manners. For example, a polymeric jacket may be disposed along the inner and/or outer surface of the reinforcing element 384. It is contemplated that a polymeric material may be extruded or heat shrunk over the reinforcing element 384. These are just examples. In some instances, the distal section 382 may be injection molded with the reinforcing element 384. In other instances, the distal section 382 may be reflowed proximally to partially extend over the proximal section 380.

Figure 6:
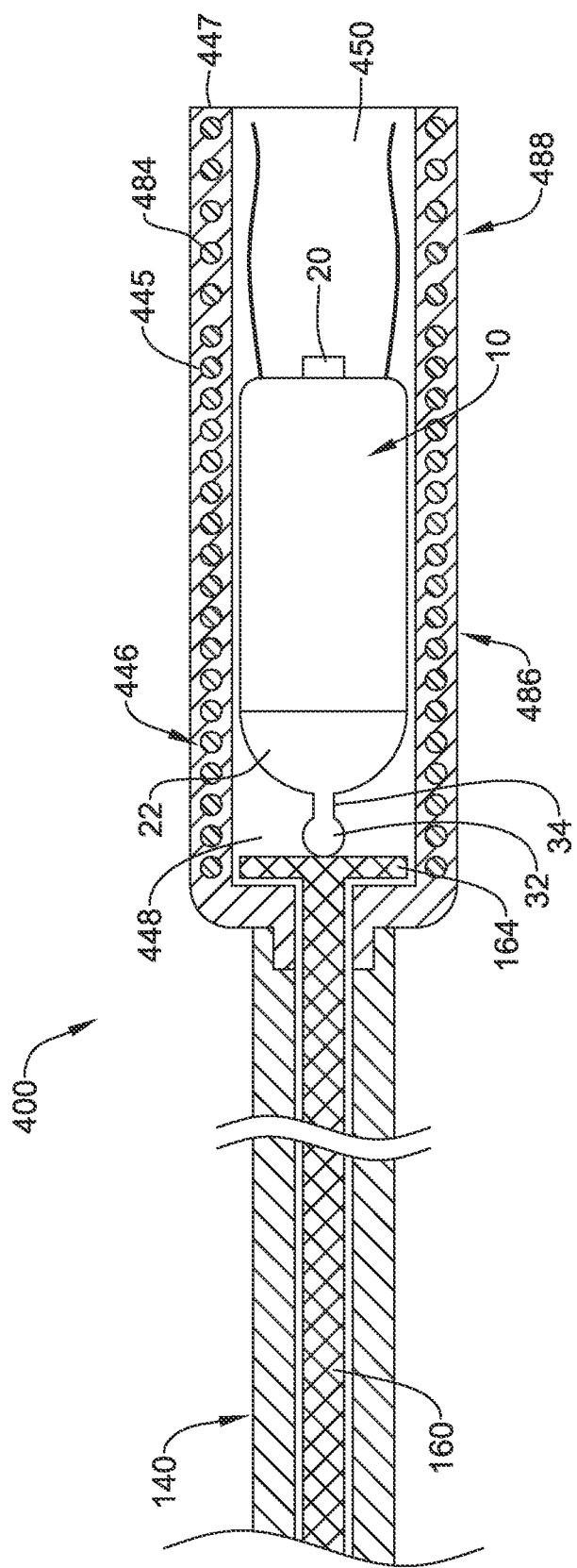
FIG. 6 is a partial cross-sectional side view of the distal portion of another illustrative delivery device, showing the implantable leadless cardiac pacing device disposed therein.

FIG. 6 illustrates a partial cross-sectional side view of the distal portion of another illustrative delivery device 400, such as a catheter, which is similar in many respects to that of the delivery device 100 shown in FIG. 2, with similar structures numbered the same. The delivery device 400 may include a proximal section 140, such as a proximal shaft, and a distal section and/or holding section 446, attached to the distal end of the proximal section 140. The distal holding section 446 may be configured to receive the implantable device 10 therein. For example, the holding section 446 may define a cavity 448 for slidably receiving the implantable device 10, and may include a distal opening 450 for slidable insertion and/or extraction of the implantable device 10 into and/or out of the cavity 448. The distal holding section 446, or portions thereof, may be configured to have portions that flex and bend while allowing the implantable device 10 to be recaptured within the distal holding section 446. Other suitable distal holding sections that are able to receive the implantable device 10 therein may also be used. Such alternative holding sections may be applied to all other embodiments shown and/or discussed herein, and others, as appropriate.

The distal holding section 446 may include a body portion 445 and a distal tip portion 447 that may, for example, be configured to be atraumatic to anatomy, such as a bumper tip. In some instances, the distal tip 447 may be made of a material that is softer than the body portion 445 of the distal holding section, although this is not required. In some cases, the distal tip 447 may include a material that has a durometer that is less than the durometer of the material of the body portion 445. Additionally, the distal tip 447 may include a shape or structure that may make it less traumatic to tissue. For example, the distal tip 447 may have a distal surface, such as a tissue contacting surface, that is rounded or includes a curvature configured to be more atraumatic to tissue.

In some embodiments, all or a portion of the distal holding section 446 may include an inner surface that may be configured to resist getting caught on the fixation mechanism 24, such as the one or more, or a plurality of hooks 26 on the device 10. For example, the distal holding section 446 may include an inner layer or coating of harder or more lubricious material that resists force applied by the fixation mechanism 24 onto the inner surface of the distal holding section 446. For example, the distal holding section 446 may include a multi-layered structure, and an inner layer may be made of a material that is harder than an outer layer.

The distal holding section 446 may further include a reinforcing element 484 covered by the polymeric body 445, such as embedded within the polymeric body 445. The reinforcing element 484 may be configured to provide a stable structure to the distal holding section 446 while still allowing the distal holding section 446 to flex and bend to facilitate retrieval of the device 10. In some instances, the reinforcing element 484 may include an embedded coil. The coil 484 may extend proximally from a point adjacent the distal tip 447. It is contemplated that the coil 484 may extend over any length of the distal holding section 446 desired. In some instances, the reinforcing element or coil 484 may be formed from stainless steel. This is just an example. In some embodiments, the reinforcing element or coil 484 may include radiopaque properties to facilitate delivery and/or retrieval of the implantable device 10. The filament or strut forming the reinforcing element or coil 484 may have any cross-sectional shape desired, such as, but not limited to, circular, square, rectangular, ovoid, polygonal, etc.

In some instances, the coil 484 may include a proximal section 486 and a distal section 488. The proximal section 486 may be formed such that the distance between adjacent windings of the coil 484 is different (e.g., less than or greater than) a distance between adjacent windings of the distal section 488. For example, the coil 484 may be more tightly wound over a length of the proximal section 486 than over a length of the distal section 488. In other embodiments, the distal section 488 may be more tightly wound than the proximal section 486. The polymeric body 445 may be formed from a material having a durometer in the range of about 20 D to about 50 D, about 30 D to about 40 D or about 35 D, for example. For example, the polymeric body 445 may be formed from a 35 D polyether block amide. This is just an example. The reinforcing element or coil 484 may provide pushability over the proximal section 486 (or tightly wound section) and flexibility over the distal section 488 (or less tightly wound section). For example, the reinforcing element 484 may be configured to provide a pushable structure resistant to collapse while still allowing the distal holding section 446 to flex and bend to facilitate retrieval of the device 10. As can be appreciated, the spacing of adjacent windings (pitch), the size, and/or shape of the coil 484 may be varied to achieve the desired characteristics. For example, a coil having a larger pitch (greater distance between adjacent windings) may be more flexible than a similarly sized and shaped coil having a smaller pitch.

While the reinforcing element 484 is described as embedded within the polymeric body 445, it is contemplated that the distal holding section 446 may be formed in other manners. For example, a polymeric jacket may be disposed along the inner and/or outer surface of the reinforcing element 484. It is contemplated that a polymeric material may be extruded or heat shrunk over the reinforcing element 484. These are just examples. In some instances, the polymeric body 445 may be injection molded with the reinforcing element 484. In some instances, the reinforcing element or coil 484 may extend from an inner surface of the distal holding section 446. This may create a helical or threaded path to engage a mating threaded region (not explicitly shown) on the implantable device 10.

Figure 7A:
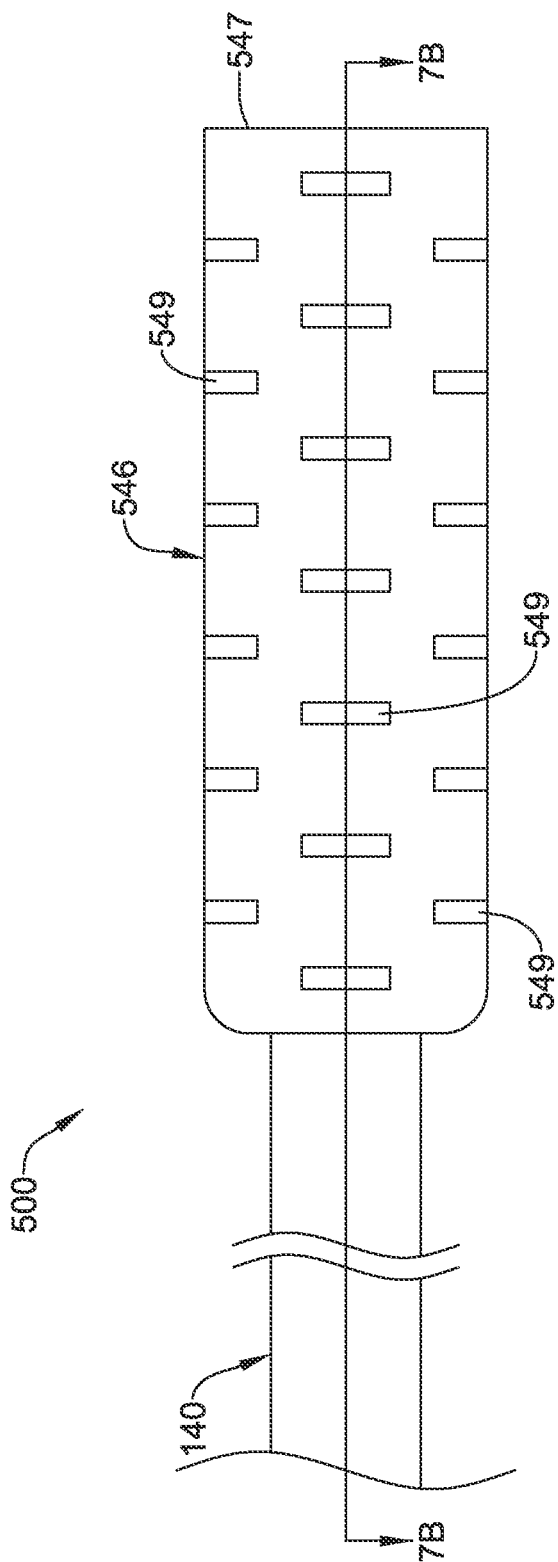
FIG. 7A is a side view of the distal portion of another illustrative delivery device.
Figure 7B:
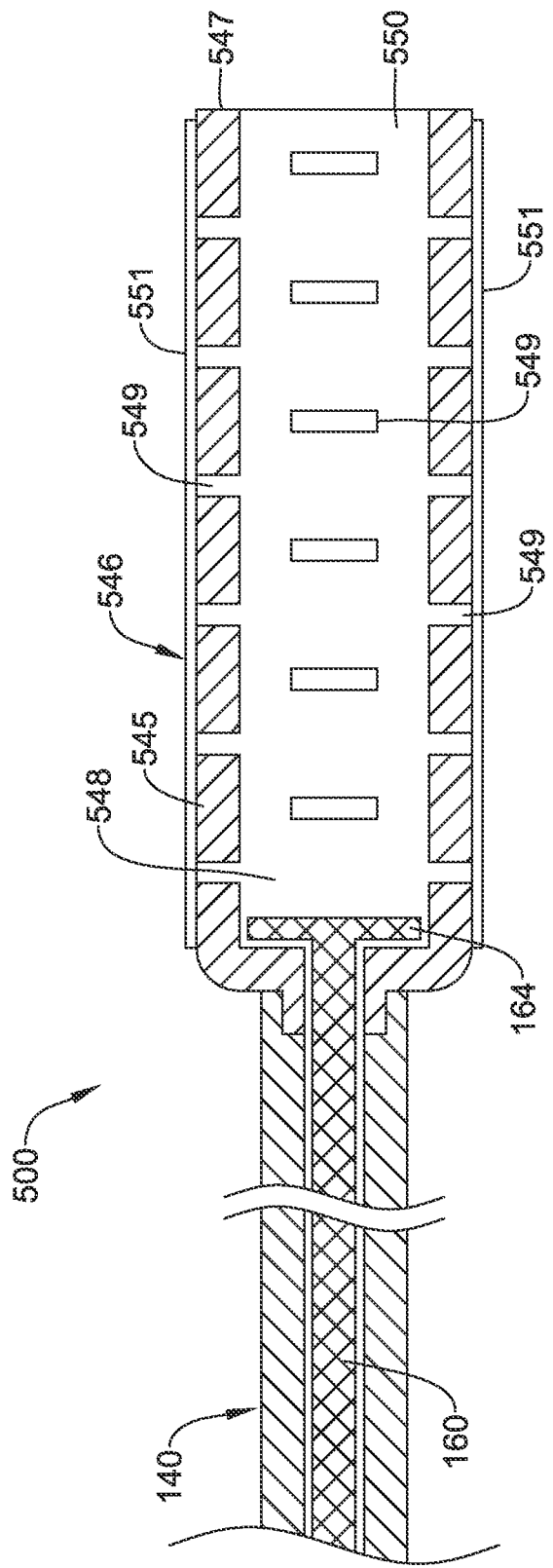
FIG. 7B is a cross-sectional side view of the distal portion of the delivery device of FIG. 7A.

FIG. 7A illustrates a side view of the distal portion of another illustrative delivery device 500, such as a catheter, which is similar in many respects to that of the delivery device 100 shown in FIG. 2, with similar structures numbered the same. FIG. 7B illustrates a cross-sectional view of the distal portion of the delivery device 500 of FIG. 7A taken at line 7B-7B. The delivery device 500 may include a proximal section 140, such as a proximal shaft, and a distal section and/or holding section 546, attached to the distal end of the proximal section 140. The distal holding section 546 may be configured to receive the implantable device 10 therein. For example, the holding section 546 may define a cavity 548 (see, e.g., FIG. 7B) for slidably receiving the implantable device 10, and may include a distal opening 550 for slidable insertion and/or extraction of the implantable device 10 into and/or out of the cavity 548. The distal holding section 546, or portions thereof, may be configured to have portions that flex and bend while allowing the implantable device 10 to be recaptured within the distal holding section 546. Other suitable distal holding sections that are able to receive the implantable device 10 therein may also be used. Such alternative holding sections may be applied to all other embodiments shown and/or discussed herein, and others, as appropriate.

The distal holding section 546 may include a body portion 545 and a distal tip portion 547 that may be, for example, configured to be atraumatic to anatomy, such as a bumper tip. In some instances, the distal tip 547 may be made of a material that is softer than the body portion 545 of the distal holding section, although this is not required. In some cases, the distal tip 547 may include a material that has a durometer that is less than the durometer of the material of the body portion 545. Additionally, the distal tip 547 may include a shape or structure that may make it less traumatic to tissue. For example, the distal tip 547 may have a distal surface, such as a tissue contacting surface, that is rounded or includes a curvature configured to be more atraumatic to tissue.

In some embodiments, all or a portion of the distal holding section 546 may include an inner surface that may be configured to resist getting caught on the fixation mechanism 24, such as the one or more, or a plurality of hooks 26 on the device 10. For example, the distal holding section 546 may include an inner layer or coating of harder or more lubricious material that resists force applied by the fixation mechanism 24 onto the inner surface of the distal holding section 546. For example, the distal holding section 546 may include a multi-layered structure, and an inner layer may be made of a material that is harder than an outer layer.

The body portion 545 may be formed from any material desired. In some instances, the body portion 545 may be formed from a material having a durometer in the range of about 60 D to about 80 D, about 65 D to about 75 D or about 70 D. The body portion 545 may include a plurality of cuts or apertures 549 to provide a degree of lateral flexibility and/or vary the stiffness along the length of the distal holding section 546. For example, the body portion 545 may include a thin wall tubular structure including one or more apertures or cuts 549, for example grooves, slits, slots, holes, openings, or the like, formed in a portion of, or along the entire length of the body portion 545. The apertures or cuts 549 can be formed in essentially any known way. For example, apertures or cuts 549 can be formed by methods such as micro-machining, saw-cutting, laser cutting, grinding, milling, casting, molding, chemically etching or treating, drilling, or other known methods, and the like.

In some embodiments, the apertures or cuts 549 may completely penetrate the body wall of the body portion 545. In other cases, only some of the apertures or cuts 549 completely penetrate the body wall. In such cases, some or all of the apertures or cuts 549 may only partially extend into the body wall of the body portion 545, either on the interior or exterior surface thereof. The shape and size of the apertures or cuts 549 can vary to achieve the desired characteristics. For example, the shape of apertures or cuts 549 can vary to include essentially any appropriate shape, such as, but not limited to square, triangular, round, rectangular, pill-shaped, oval, polygonal, diamond, elongate, irregular, spiral (which may or may not vary in pitch), or other suitable means or the like, and may include rounded or squared edges, and can be variable in length and width, total open area, and the like. In some instances, the apertures or cuts 549 may have a generally rectangular shape with the major length of the rectangle extending generally parallel to a longitudinal axis of the proximal section 140. In other instances, the apertures or cuts 549 may have a major length that extends generally perpendicular to the longitudinal axis of the proximal section 140 or at an oblique angle to the longitudinal axis of the proximal section 140.

In some embodiments, some adjacent apertures or cuts 549 can be formed such that they include portions that overlap with each other about the circumference of the body portion B545. In other embodiments, some adjacent apertures or cuts 549 can be disposed such that they do not necessarily overlap with each other, but are disposed in a pattern that provides the desired degree and/or direction of lateral flexibility. For example, the apertures or cuts 549 can be arranged in a symmetrical pattern, such as being disposed essentially equally on opposite sides about the circumference of the body portion 545, or equally spaced along the length of the body portion 545.

As can be appreciated, the spacing, arrangement, and/or orientation of the apertures or cuts 549 can be varied to achieve the desired characteristics. For example, the number, proximity (to one another), density, size, shape and/or depth of the apertures or cuts 549 along the length of the body portion 545 may vary in either a stepwise fashion or continuously, depending upon the desired characteristics. For example, the number or proximity of apertures or cuts 549 to one another near one end of the body portion 545 may be high, while the number or proximity of apertures or cuts 549 to one another at another longitudinal location along the body portion 545 may be relatively low. In the some embodiments, portions closer to the distal tip 547 may include a greater density of apertures or cuts 549, while proximal regions of the body portion 545 may include a lesser density of apertures or cuts 549, or may even be devoid of any apertures or cuts 549. As such, the portions of the distal holding section 546 closer to the distal tip 547 can have a greater degree of lateral flexibility relative to proximal regions of the distal holding section 546.

The distal holding section 546 may further include a thin coating or jacket 551 (see, e.g. FIG. 7B) on an inner and/or outer surface of the body portion 545. In order to more clearly illustrate the apertures or cuts 549, the coating 551 has been omitted from FIG. 7A. In some embodiments, the coating 551 may be an ionically permeable coating. This may allow for electrical communication there through forming a conductive pathway. Such a conductive pathway may allow for conductive communication between electrodes 20, 22 on the device 10 (not explicitly shown) through the distal opening 550 and the apertures or cuts 549 respectively, while the device is housed within the cavity 548. Such communication may allow the device 10 to be tested prior to being released or delivered out of the cavity 548. The coating 551 may also allow a contrast agent to be delivered through a lumen of the delivery device 500 and exit through the distal opening 550 without exiting through the apertures or cuts 549.

Figure 8A:
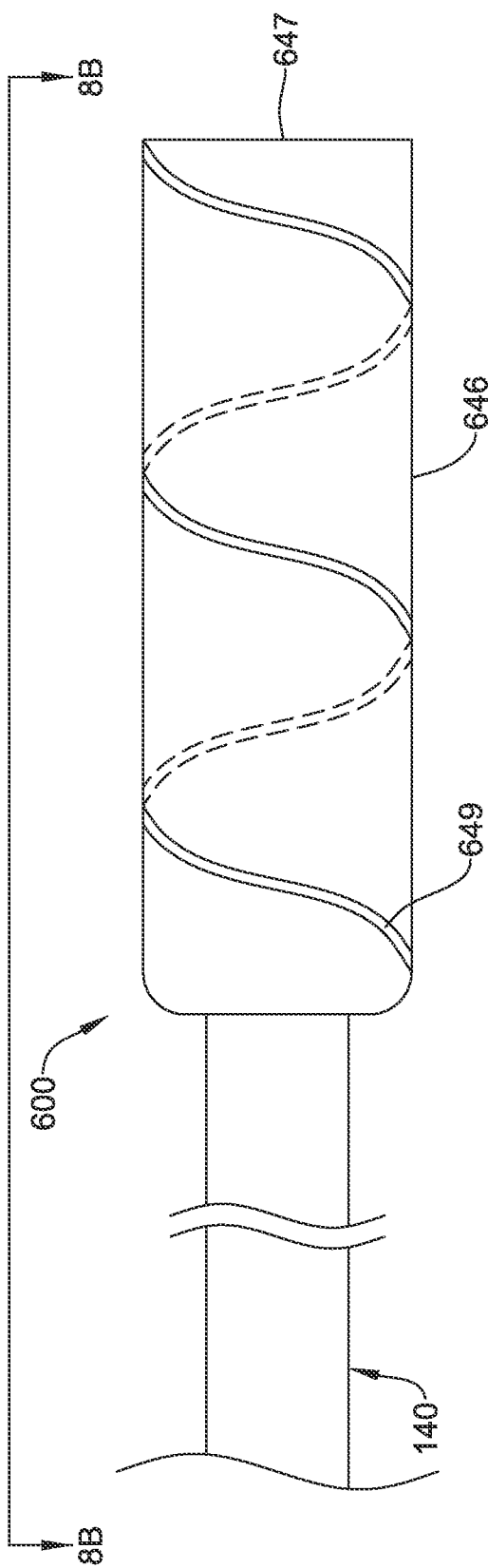
FIG. 8A is a side view of the distal portion of another illustrative delivery device.
Figure 8B:
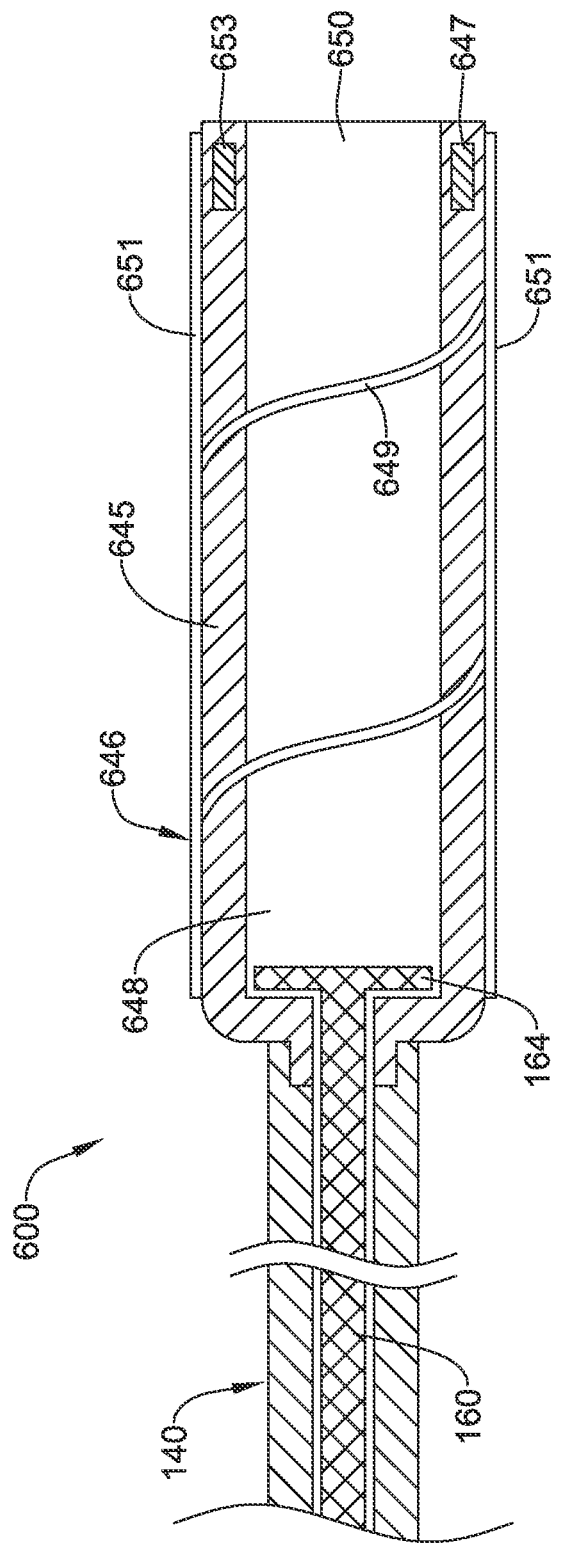
FIG. 8B is a cross-sectional side view of the distal portion of the delivery device of FIG. 8A.

FIG. 8A illustrates a side view of the distal portion of another illustrative delivery device 600, such as a catheter, which is similar in many respects to that of the delivery device 100 shown in FIG. 2, with similar structures numbered the same. FIG. 8B illustrates a cross-sectional view of the distal portion of the delivery device 600 of FIG. 8A taken at line 8B-8B. The delivery device 600 may include a proximal section 140, such as a proximal shaft, and a distal section and/or holding section 646, attached to the distal end of the proximal section 140. The distal holding section 646 may be configured to receive the implantable device 10 therein. For example, the holding section 646 may define a cavity 648 (see, e.g., FIG. 8B) for slidably receiving the implantable device 10, and may include a distal opening 650 for slidable insertion and/or extraction of the implantable device 10 into and/or out of the cavity 648. The distal holding section 646, or portions thereof, may be configured to have portions that flex and bend while allowing the implantable device 10 to be recaptured within the distal holding section 646. Other suitable distal holding sections that are able to receive the implantable device 10 therein may also be used. Such alternative holding sections may be applied to all other embodiments shown and/or discussed herein, and others, as appropriate.

The distal holding section 646 may include a body portion 645 and a distal tip portion 647 that may, for example, be configured to be atraumatic to anatomy, such as a bumper tip. In some instances, the distal tip 647 may be made of a material that is softer than the body portion 645 of the distal holding section, although this is not required. In some cases, the distal tip 647 may include a material that has a durometer that is less than the durometer of the material of the body portion 645. Additionally, the distal tip 647 may include a shape or structure that may make it less traumatic to tissue. For example, the distal tip 647 may have a distal surface, such as a tissue contacting surface, that is that is rounded or includes a curvature configured to be more atraumatic to tissue.

In some embodiments, all or a portion of the distal holding section 646 may include an inner surface that may be configured to resist getting caught on the fixation mechanism 24, such as the one or more, or a plurality of hooks 26 on the device 10. For example, the distal holding section 646 may include an inner layer or coating of harder or more lubricious material that resists force applied by the fixation mechanism 24 onto the inner surface of the distal holding section 646. For example, the distal holding section 646 may include a multi-layered structure, and an inner layer may be made of a material that is harder than an outer layer.

The body portion 645 may be formed from any material desired. In some instances, the body portion 645 may be formed from a material having a durometer in the range of about 60 D to about 80 D, about 65 D to about 75 D or about 70 D. The body portion 645 may include one or more spiral cuts or apertures 649 to provide a degree of lateral flexibility and/or vary the stiffness along the length of the distal holding section 646. For example, the body portion 645 may include a thin wall tubular structure including one or more spiral apertures or cuts 649, for example grooves, slits, slots, or the like, formed in a portion of, or along the entire length of, the body portion 645. The apertures or cuts 649 can be formed in essentially any known way. For example, the spiral aperture or cut 649 can be formed by methods such as micro-machining, saw-cutting, laser cutting, grinding, milling, casting, molding, chemically etching or treating, drilling, or other known methods, and the like.

In some embodiments, the aperture or cut 649 may completely penetrate the body wall of the body portion 645. In other cases, the aperture or cut 649 may not completely penetrate the body wall of the body portion 645, or only some or a portion of the aperture or cut 649 completely penetrates the body wall. In such cases, some or all of the aperture or cut 649 may only partially extend into the body wall of the body portion 645, either on the interior or exterior surface thereof. The shape and size of the aperture or cut 649 can vary to achieve the desired characteristics. For example, the thickness of the aperture or cut 649 can vary as well as the pitch to achieve the desired flexibility. For example, an aperture or cut 649 having a smaller pitch (e.g. smaller distance between adjacent windings) may result in a more flexible distal holding section 646 than an aperture or cut 649 having a larger pitch. It is further contemplated the body portion 645 may include more than one spiral aperture or cut 649.

As can be appreciated, the spacing, arrangement, and/or orientation of the aperture(s) or cut(s) 649 can be varied to achieve the desired characteristics. For example, the number, proximity (to one another), density, size, shape and/or depth of the aperture(s) or cut(s) 649 along the length of the body portion 645 may vary in either a stepwise fashion or continuously, depending upon the desired characteristics. For example, the pitch of the windings of the aperture(s) or cut(s) 649 to one another near one end of the body portion 645 may be small, while the pitch of the windings of the aperture(s) or cut(s) 649 to one another at another longitudinal location along the body portion 645 may be relatively large. In the some embodiments, portions closer to the distal tip 647 may include a smaller pitched aperture or cut 649, while the body portion 645 proximal regions may include a larger pitched of aperture or cut 649, or may even be devoid of any apertures or cuts 649. As such, the portions of the distal holding section 646 closer to the distal tip 647 can have a greater degree of lateral flexibility relative to distal holding section 646 proximal regions.

The distal holding section 646 may further include a thin coating or jacket 651 (see, e.g. FIG. 8B) on an inner and/or outer surface of the body portion 645. In order to more clearly illustrate the apertures or cuts 649, the coating 651 has been omitted from FIG. 8A. In some embodiments, the coating 651 may be an ionically permeable coating. This may allow for electrical communication there through forming a conductive pathway. Such a conductive pathway may allow for conductive communication between electrodes 20, 22 on the device 10 (not explicitly shown) through the distal opening 650 and the spiral apertures or cuts 649 respectively, while the device is housed within the cavity 648. Such communication may allow the device 10 to be tested prior to being released or delivered out of the cavity 648. The coating 651 may also allow a contrast agent to be delivered through a lumen of the delivery device 600 and exit through the distal opening 650 without exiting through the apertures or cuts 649.

In some instances, the distal holding section 646 may include a reinforcing element 653 positioned adjacent to the distal tip 647. The reinforcing element 653 may have a "C" shape configured to allow the distal end region of the distal holding section 646 to expand. For example, the body portion 645 may include a fold of excess material adjacent to the reinforcing element 653 to allow the distal end region to expand and accommodate an implantable device 10. While the reinforcing element 653 is illustrated as having a generally rectangular cross-section, it is contemplated that the reinforcing element 653 may have any cross-sectional shape desired, such as, but not limited to, square, circular, oval, polygonal, etc.

Figure 9:
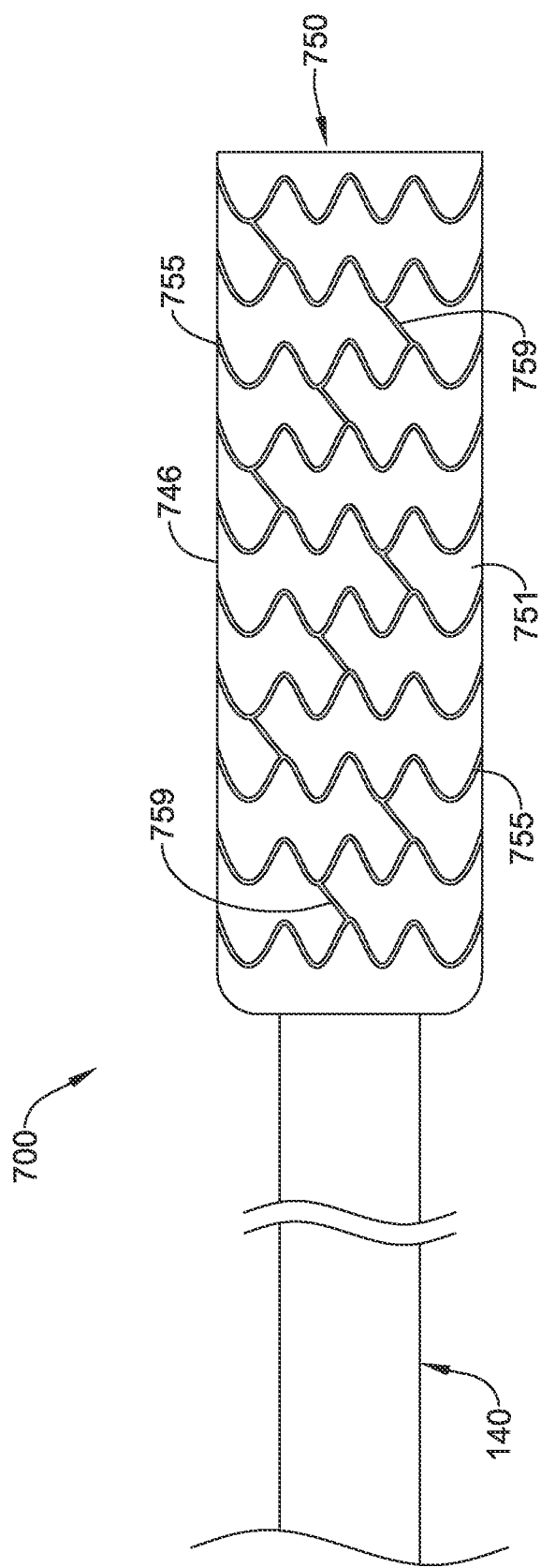
FIG. 9 is a side view of the distal portion of another illustrative delivery device.

FIG. 9 illustrates a side view of the distal portion of another illustrative delivery device 700, such as a catheter, which is similar in many respects to that of the delivery device 100 shown in FIG. 2, with similar structures numbered the same. The delivery device 700 may include a proximal section 140, such as a proximal shaft, and a distal section and/or holding section 746, attached to the distal end of the proximal section 140. The distal holding section 746 may be configured to receive the implantable device 10 therein. For example, the holding section 746 may define a cavity (not explicitly shown) for slidably receiving the implantable device 10, and may include a distal opening 750 for slidable insertion and/or extraction of the implantable device 10 into and/or out of the cavity. The distal holding section 746, or portions thereof, may be configured to have portions that flex and bend while allowing the implantable device 10 to be recaptured within the distal holding section 746. Other suitable distal holding sections that are able to receive the implantable device 10 therein may also be used. Such alternative holding sections may be applied to all other embodiments shown and/or discussed herein, and others, as appropriate.

In some embodiments, all or a portion of the distal holding section 746 may include an inner surface that may be configured to resist getting caught on the fixation mechanism 24, such as the one or more, or a plurality of hooks 26 on the device 10. For example, the distal holding section 746 may include an inner layer or coating of harder or more lubricious material that resists force applied by the fixation mechanism 24 onto the inner surface of the distal holding section 746. For example, the distal holding section 746 may include a multi-layered structure, and an inner layer may be made of a material that is harder than an outer layer.

The distal holding section 746 may be formed from any material desired. In some instances, the distal holding section 746 may be formed from a material having a durometer in the range of about 60 D to about 80 D, about 65 D to about 75 D or about 70 D. In some instances, the distal holding section 746 may comprise a plurality of interconnected stent-like struts 755. For example, the distal holding section 746 may be formed from a generally tubular member and altered to form a desired pattern. For example, the pattern of struts 755 and connectors 759 may be formed by methods such as micro-machining, saw-cutting, laser cutting, grinding, milling, casting, molding, chemically etching or treating, drilling, or other known methods, and the like. While the distal holding section 746 is illustrated as having an open cell, generally stent-like, structure it is contemplated that the distal holding section 746 may be formed to have any of a number of different configurations. In some embodiments, the distal holding section 746 may be formed from a plurality of interconnected generally circumferentially extending struts 755. The struts 755 may be connected by one or more connectors 759. It is contemplated that the struts 755 in combination with the connectors 759 may form a cellular configuration with each cell having any shape desired, such as, but not limited to: circular, square, oval, rectangular, polygonal, etc. In some instances, the distal holding section 746 may be formed from a number of generally longitudinally extending tines or may be formed from one or more filaments that may be woven, braided, knotted, etc. These are just examples.

As can be appreciated, the spacing, arrangement, and/or orientation of the struts 755 or connectors 759 can be varied to achieve the desired characteristics. For example, the number, proximity (to one another), density, size, and/or shape of the struts 755 or connectors 759 along the length of the distal holding section 746 may vary in either a stepwise fashion or consistently, depending upon the desired characteristics. For example, closely positioned adjacent struts 755 may have less flexibility than adjacent struts 755 positioned further from one another.

The distal holding section 746 may further include a thin coating or jacket 751 on an inner and/or outer surface of the distal holding section 746. In order to more clearly illustrate the struts 755 and connectors 759, the coating 751 is illustrated as disposed on an inner surface of the distal holding section 746. However, the coating 751 may be disposed over an outer surface of the distal holding section 746. In some embodiments, the coating 751 may be an ionically permeable coating. This may allow for electrical communication there through forming a conductive pathway. Such a conductive pathway may allow for conductive communication between electrodes 20, 22 on the device 10 (not explicitly shown) through the distal opening 750 and the regions between adjacent struts 755 respectively, while the device is housed within the cavity. Such communication may allow the device 10 to be tested prior to being released or delivered out of the cavity. The coating 751 may also allow a contrast agent to be delivered through a lumen of the delivery device 700 and exit through the distal opening 50 without exiting through the regions between adjacent struts 755.

Figure 10A:
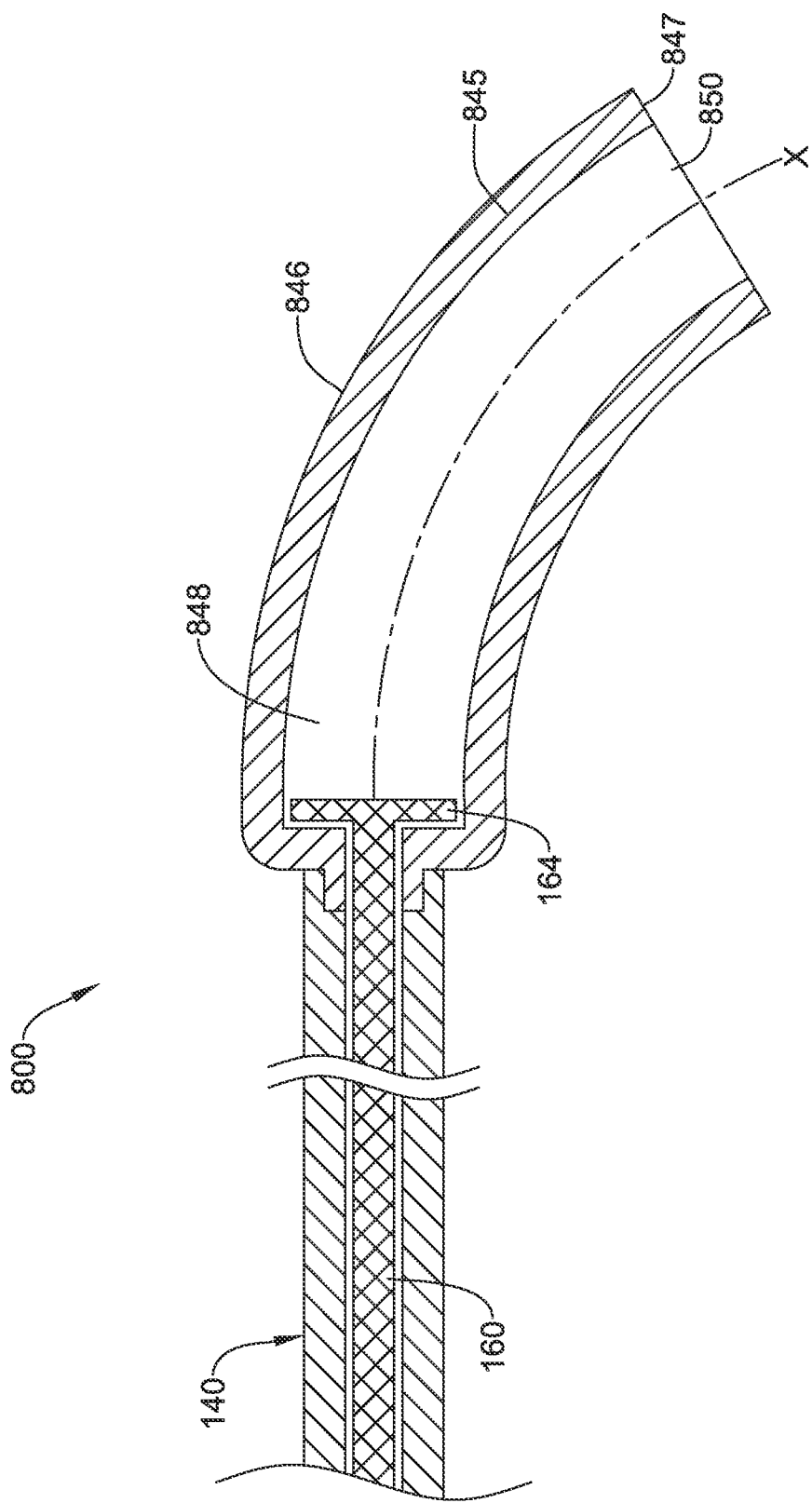
FIG. 10A is a cross-sectional side view of the distal portion of another illustrative delivery device.
Figure 10B:
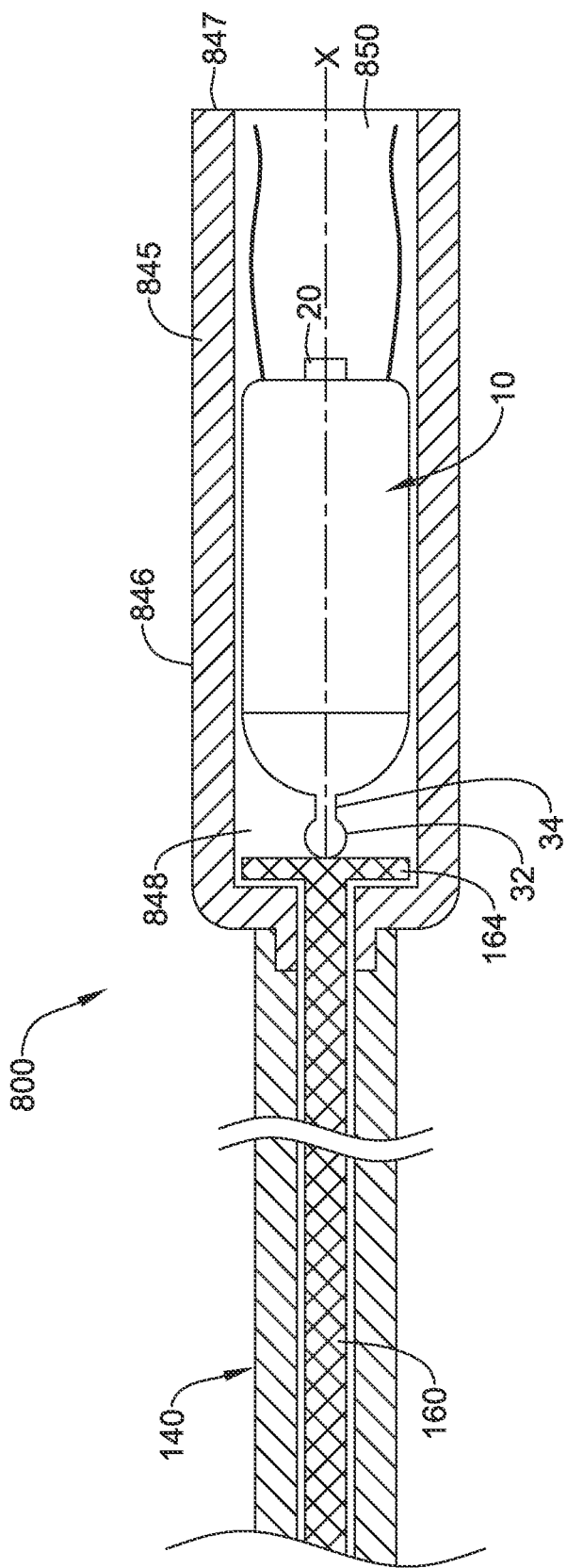
FIG. 10B is a cross-sectional side view of the distal portion of the delivery device of FIG. 10B, showing the implantable leadless cardiac pacing device disposed therein.

FIGS. 10A and 10B illustrate a partial cross-sectional side view of the distal portion of another illustrative delivery device 800, such as a catheter, which is similar in many respects to that of the delivery device 100 shown in FIG. 2, with similar structures numbered the same. The delivery device 800 may include a proximal section 140, such as a proximal shaft, and a distal section and/or holding section 846, attached to the distal end of the proximal section 140. The distal holding section 846 may be configured to receive the implantable device 10 therein. For example, the holding section 846 may define a cavity 848 for slidably receiving the implantable device 10, and may include a distal opening 850 for slidable insertion and/or extraction of the implantable device 10 into and/or out of the cavity 848. The distal holding section 846, or portions thereof, may be configured to have portions that flex and bend while allowing the implantable device 10 to be recaptured within the distal holding section 846. Other suitable distal holding sections that are able to receive the implantable device 10 therein may also be used. Such alternative holding sections may be applied to all other embodiments shown and/or discussed herein, and others, as appropriate.

The distal holding section 846 may include a body portion 845 and a distal tip portion 847 that may, for example, be configured to be atraumatic to anatomy, such as a bumper tip. In some instances, the distal tip 847 may be made of a material that is softer than the body portion 845 of the distal holding section 846, although this is not required. In some cases, the distal tip 847 may include a material that has a durometer that is less than the durometer of the material of the body portion 845. Additionally, the distal tip 847 may include a shape or structure that may make it less traumatic to tissue. For example, the distal tip 847 may have a distal surface, such as a tissue contacting surface, that is that is rounded or includes a curvature configured to be more atraumatic to tissue.

In some embodiments, all or a portion of the distal holding section 846 may include an inner surface that may be configured to resist getting caught on the fixation mechanism 24, such as the one or more, or a plurality of hooks 26 on the device 10. For example, the distal holding section 846 may include an inner layer or coating of harder or more lubricious material that resists force applied by the fixation mechanism 24 onto the inner surface of the distal holding section 846. For example, the distal holding section 846 may include a multi-layered structure, and an inner layer may be made of a material that is harder than an outer layer.

The distal holding section 846 may be formed to include a predefined or fixed curve portion(s) along a length thereof when an implantable device 10 is not disposed within the cavity 848, as shown in FIG. 10A. In other words, the central axis X of the distal holding section 846 may be curved when the distal holding section 846 is in an equilibrium state. This may help align the distal opening 850 with an implantable device 10 in the event it needs to be recaptured within the distal holding section 846. As the implantable device 10 is recaptured (or during initial loading and delivery of the implantable device) the distal holding section 846 may straighten to extend generally parallel with a longitudinal axis of the proximal section 140. In other words, implantable device 10 (which may include a rigid housing) may exert a force on the distal holding section 846 to straighten the distal holding section 846 away from its equilibrium curved state when inserted therein. Thus, the forces exerted by the implantable device 10 on the interior of the distal holding section 846 may straighten the central axis X to be generally parallel with the longitudinal axis of the implantable device 10 and the push member 160, as shown in FIG. 10B.

In some instances, the distal holding section 846 may be formed from a shape memory material, although this is not required. In broad terms, shape memory polymers behave similarly to shape memory alloys such as the nickel-titanium alloys commonly referred to as nitinol. Shape memory polymers may be formed in a parent (or remembered) shape. The shape memory polymer may be temporarily deformed into another shape by heating the polymer above the transition temperature (in some instances this may be the glass transition temperature or the melting temperature), changing the shape of the polymer, and cooling the polymer while maintaining it in the temporary shape. An external stimulus, such as, but not limited to, heat, may be used to return the shape memory polymer to the remembered shape from the temporary shape. The shape memory polymer may be selected to be biocompatible.

Figure 11:
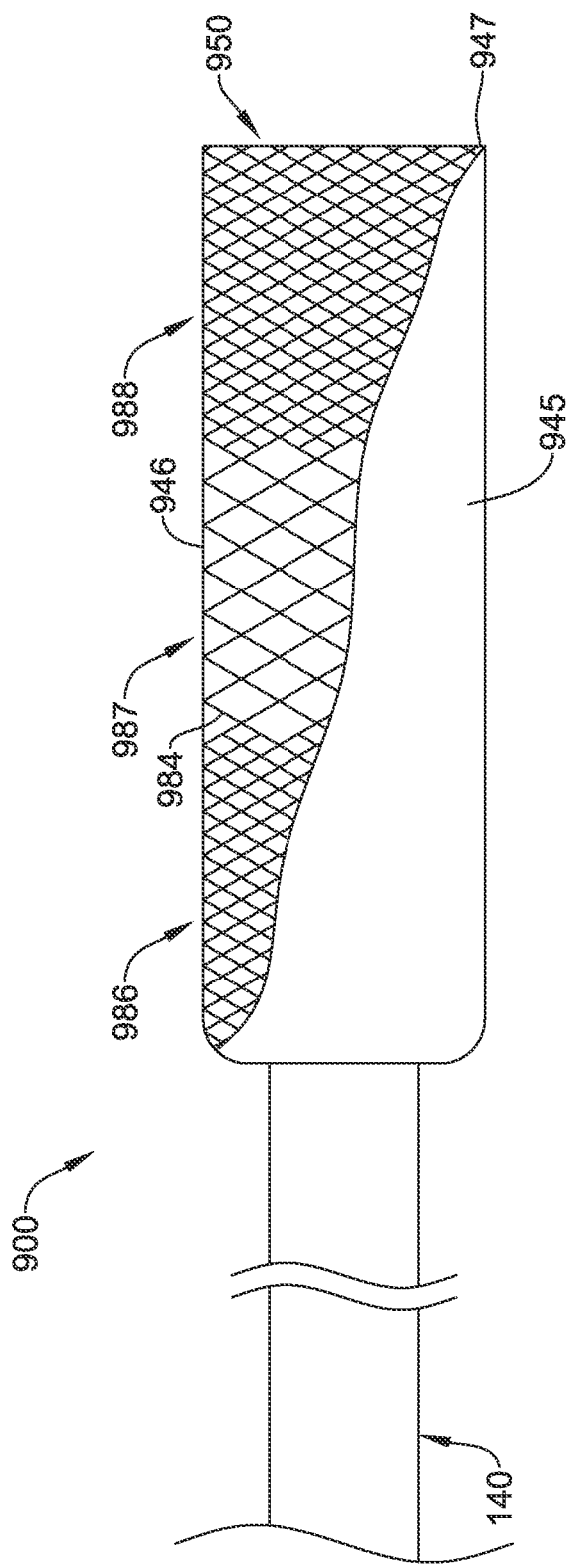
FIG. 11 is a partial sectional side view of the distal portion of another illustrative delivery device.

FIG. 11 illustrates a side view in partial section of the distal portion of another illustrative delivery device 900, such as a catheter, which is similar in many respects to that of the delivery device 100 shown in FIG. 2, with similar structures numbered the same. The delivery device 900 may include a proximal section 140, such as a proximal shaft, and a distal section and/or holding section 946, attached to the distal end of the proximal section 140. The distal holding section 946 may be configured to receive the implantable device 10 therein. For example, the holding section 946 may define a cavity (not explicitly shown) for slidably receiving the implantable device 10, and may include a distal opening 950 for slidable insertion and/or extraction of the implantable device 10 into and/or out of the cavity. The distal holding section 946, or portions thereof, may be configured to have portions that flex and bend while allowing the implantable device 10 to be recaptured within the distal holding section 946. Other suitable distal holding sections that are able to receive the implantable device 10 therein may also be used. Such alternative holding sections may be applied to all other embodiments shown and/or discussed herein, and others, as appropriate.

Figure 11A:
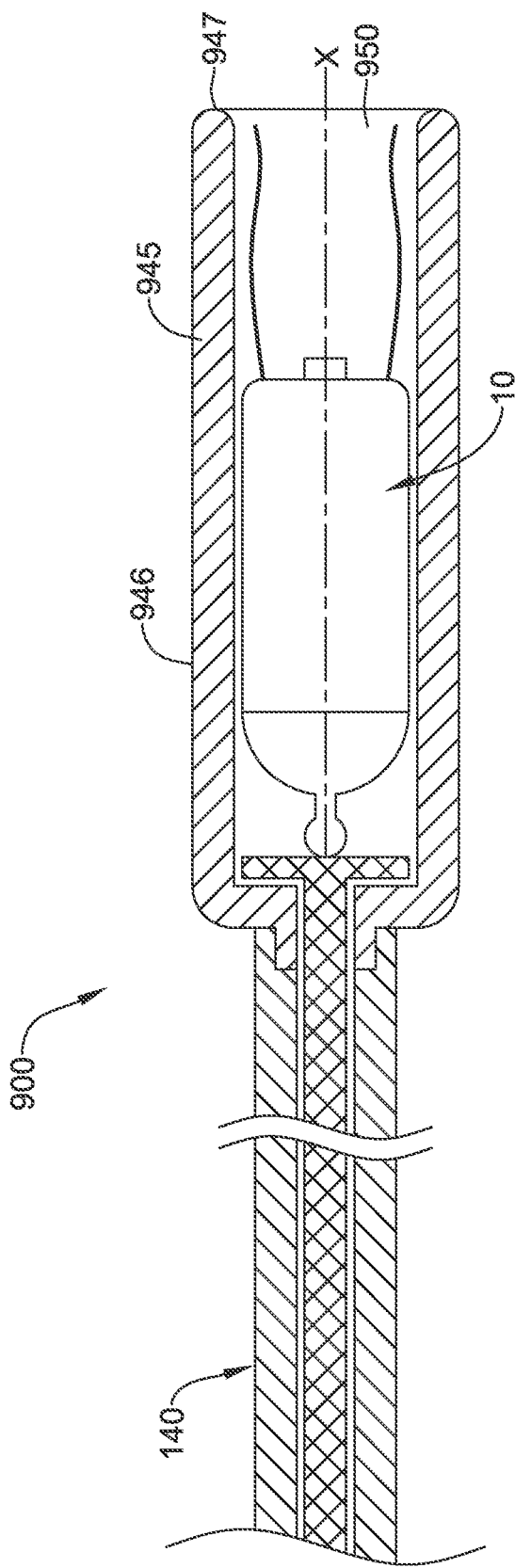
FIG. 11A is a cross-sectional side view of the distal portion of the delivery device of FIG. 11, showing the implantable leadless cardiac pacing device disposed therein.

The distal holding section 946 may include a body portion 945 and a distal tip portion 947 that may, for example, be configured to be atraumatic to anatomy, such as a bumper tip. In some instances, the distal tip 947 may be made of a material that is softer than the body portion 945 of the distal holding section, although this is not required. In some cases, the distal tip 947 may include a material that has a durometer that is less than the durometer of the material of the body portion 945. Additionally, the distal tip 947 may include a shape or structure that may make it less traumatic to tissue. For example, the distal tip 947 may have a distal surface, such as a tissue contacting surface, that is rounded or includes a curvature configured to be more atraumatic to tissue, as seen in FIG. 11A.

In some embodiments, all or a portion of the distal holding section 946 may include an inner surface that may be configured to resist getting caught on the fixation mechanism 24, such as the one or more, or a plurality of hooks 26 on the device 10. For example, the distal holding section 946 may include an inner layer or coating of harder or more lubricious material that resists force applied by the fixation mechanism 24 onto the inner surface of the distal holding section 946. For example, the distal holding section 946 may include a multi-layered structure, and an inner layer may be made of a material that is harder than an outer layer.

The distal holding section 946 may further include a reinforcing element 984 covered by the polymeric body 945, such as embedded within the polymeric body 945. A portion of the polymeric body 945 is shown in partial section to more clearly illustrate the reinforcing element 984. The reinforcing element 984 may be configured to provide a stable structure to the distal holding section 946 while still allowing the distal holding section 946 to flex and bend to facilitate retrieval of the device 10. In some instances, the reinforcing element 984 may include an embedded braided element formed from two or more filaments. While the reinforcing element 984 is described as braided, it is contemplated that the reinforcing element may be woven, wound, or otherwise intertwined. The braid 984 may extend proximally from a point adjacent the distal tip 947. It is contemplated that the braid 984 may extend over any length of the distal holding section 946 desired. In some instances, the reinforcing element or braid 984 may be formed from a metal, a metal alloy, such as nitinol, or a polymeric material. These are just examples. In some embodiments, the reinforcing element or braid 984 may include radiopaque properties to facilitate delivery and/or retrieval of the implantable device 10. The filaments or struts forming the reinforcing element or braid 984 may have any cross-sectional shape desired, such as, but not limited to, circular, square, rectangular, ovoid, polygonal, etc.

In some instances, the braid 984 may include a proximal section 986, a distal section 988, and an intermediate section 987 disposed between the proximal section 986 and the distal section 988. The proximal section 986, intermediate section 987 and distal section 988 may each be formed such that the pitch of the braided elements between adjacent windings of the braid 984 is different (e.g., less than or greater than) a pitch between adjacent windings of the other sections. For example, the proximal section 986 may have a first pitch, the intermediate section 987 may have a second pitch which may be different than the first pitch, and the distal section 988 may have a third pitch which may different than the first and/or second pitches, although this is not required. For example, the braid 984 may be more tightly formed over a length of the proximal section 986 and the distal section 988 than over a length of the intermediate section 987. It is contemplated this arrangement may allow the distal holding section 946 to flex or bend to a greater extent over the less tightly formed region, such as the intermediate section 987 in FIG. 11. This is just an example. Other configurations are contemplated. For example, in other embodiments, the intermediate section 987 may be more tightly wound than the proximal section 986 and the distal section 988. It is further contemplated that the proximal section 986 and the distal section 988 may have pitches different from one another. In some instances, the proximal section 986 may be more tightly wound or formed (e.g. have a smaller pitch) than the distal section 988. The reverse configuration is also contemplated.

The polymeric body 945 may be formed from a material having a durometer in the range of about 20 D to about 50 D, about 30 D to about 40 D or about 35 D, for example. For example, the polymeric body 945 may be formed from a 35 D polyether block amide. This is just an example. The reinforcing element or braid 984 may provide pushability over the proximal section 986 and/or distal section 988 (or tightly wound section) and flexibility over the intermediate section 987 (or less tightly wound section). For example, the reinforcing element 984 may be configured to provide a pushable structure resistant to collapse while still allowing the distal holding section 946 to flex and bend to facilitate retrieval of the device 10. As can be appreciated, the spacing of adjacent windings (pitch), the size, and/or shape of the braid 984 may be varied to achieve the desired characteristics. For example, a braid having a larger pitch (greater distance between adjacent windings) may be more flexible than a similarly sized and shaped braid having a smaller pitch.

While the reinforcing element 984 is described as embedded within the polymeric body 945, it is contemplated that the distal holding section 946 may be formed in other manners. For example, a polymeric jacket may be disposed along the inner and/or outer surface of the reinforcing element 984. It is contemplated that a polymeric material may be extruded or heat shrunk over the reinforcing element 984. These are just examples. In some instances, the polymeric body 945 may be injection molded with the reinforcing element 984. In some instances, the reinforcing element or braid 984 may extend from an inner surface of the distal holding section 946. This may create a helical or threaded path to engage a mating threaded region (not explicitly shown) on the implantable device 10.

In some instances, the distal holding section 946 may include an additional reinforcing element (not explicitly shown) positioned adjacent to the distal tip 947. The reinforcing element may have a "C" shape configured to allow the distal end region of the distal holding section 946 to expand. For example, the body portion 945 may include a fold of excess material adjacent to the reinforcing element to allow the distal end region to expand and accommodate an implantable device 10. In some instances, the additional reinforcing element may have a generally rectangular cross-section. In other instances, it is contemplated that the reinforcing element may have any cross-sectional shape desired, such as, but not limited to, square, circular, oval, polygonal, etc. The additional reinforcing element may be formed from a radiopaque material or be doped with a radiopaque material.

Figure 12:
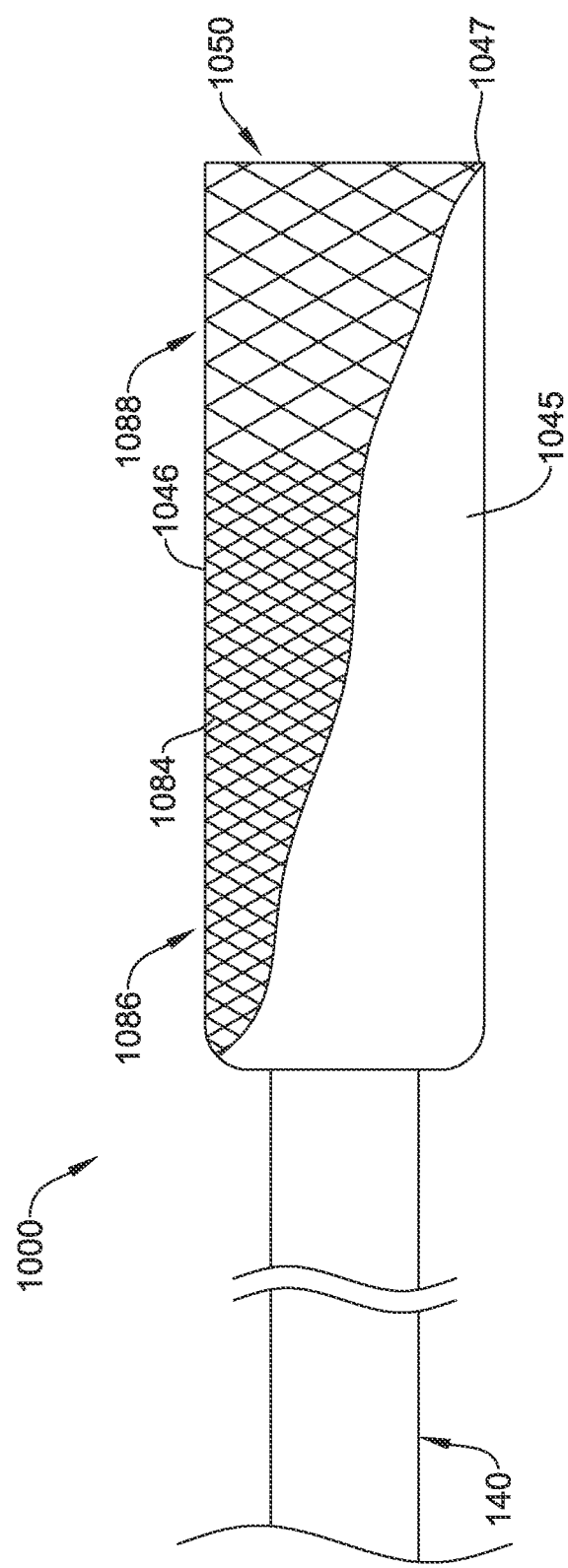
FIG. 12 is a partial sectional side view of the distal portion of another illustrative delivery device.

FIG. 12 illustrates a side view in partial section of the distal portion of another illustrative delivery device 1000, such as a catheter, which is similar in many respects to that of the delivery device 100 shown in FIG. 2, with similar structures numbered the same. The delivery device 1000 may include a proximal section 140, such as a proximal shaft, and a distal section and/or holding section 1046, attached to the distal end of the proximal section 140. The distal holding section 1046 may be configured to receive the implantable device 10 therein. For example, the holding section 1046 may define a cavity (not explicitly shown) for slidably receiving the implantable device 10, and may include a distal opening 1050 for slidable insertion and/or extraction of the implantable device 10 into and/or out of the cavity. The distal holding section 1046, or portions thereof, may be configured to have portions that flex and bend while allowing the implantable device 10 to be recaptured within the distal holding section 1046. Other suitable distal holding sections that are able to receive the implantable device 10 therein may also be used. Such alternative holding sections may be applied to all other embodiments shown and/or discussed herein, and others, as appropriate.

The distal holding section 1046 may include a body portion 1045 and a distal tip portion 1047 that may, for example, be configured to be atraumatic to anatomy, such as a bumper tip. In some instances, the distal tip 1047 may be made of a material that is softer than the body portion 1045 of the distal holding section, although this is not required. In some cases, the distal tip 1047 may include a material that has a durometer that is less than the durometer of the material of the body portion 1045. Additionally, the distal tip 1047 may include a shape or structure that may make it less traumatic to tissue. For example, the distal tip 1047 may have a distal surface, such as a tissue contacting surface, that is rounded or includes a curvature configured to be more atraumatic to tissue.

In some embodiments, all or a portion of the distal holding section 1046 may include an inner surface that may be configured to resist getting caught on the fixation mechanism 24, such as the one or more, or a plurality of hooks 26 on the device 10. For example, the distal holding section 1046 may include an inner layer or coating of harder or more lubricious material that resists force applied by the fixation mechanism 24 onto the inner surface of the distal holding section 1046. For example, the distal holding section 1046 may include a multi-layered structure, and an inner layer may be made of a material that is harder than an outer layer.

The distal holding section 1046 may further include a reinforcing element 1084 covered by the polymeric body 1045, such as embedded within the polymeric body 1045. A portion of the polymeric body 1045 is shown in partial section to more clearly illustrate the reinforcing element 1084. The reinforcing element 1084 may be configured to provide a stable structure to the distal holding section 1046 while still allowing the distal holding section 1046 to flex and bend to facilitate retrieval of the device 10. In some instances, the reinforcing element 1084 may include an embedded braided element formed from two or more filaments. While the reinforcing element 1084 is described as braided, it is contemplated that the reinforcing element may be woven, wound, or otherwise intertwined. The braid 1084 may extend proximally from a point adjacent the distal tip 1047. It is contemplated that the braid 1084 may extend over any length of the distal holding section 1046 desired. In some instances, the reinforcing element or braid 1084 may be formed from a metal, a metal alloy, such as nitinol, or a polymeric material. These are just examples. In some embodiments, the reinforcing element or braid 1084 may include radiopaque properties to facilitate delivery and/or retrieval of the implantable device 10. The filaments or struts forming the reinforcing element or braid 1084 may have any cross-sectional shape desired, such as, but not limited to, circular, square, rectangular, ovoid, polygonal, etc.

In some instances, the braid 1084 may include a proximal section 1086 and a distal section 1088. The proximal section 1086 and the distal section 1088 may each be formed such that the pitch of the braided elements between adjacent windings of the braid 1084 is different (e.g., less than or greater than) a pitch between adjacent windings of the other section. For example, the braid 1084 may have a first pitch, or be more tightly formed over a length of the proximal section 1086 than the distal section 1088, which may have a second pitch. It is contemplated this arrangement may allow the distal holding section 1046 to flex or bend to a greater extent over the less tightly formed region, such as the distal section 1088 in FIG. 12. This is just an example. Other configurations are contemplated. For example, in other embodiments, the distal section 1088 may be more tightly wound than the proximal section 1086.

The polymeric body 1045 may be formed from a material having a durometer in the range of about 20 D to about 50 D, about 30 D to about 40 D or about 35 D, for example. For example, the polymeric body 1045 may be formed from a 35 D polyether block amide. This is just an example. The reinforcing element or braid 1084 may provide pushability over the proximal section 1086 (or tightly wound section) and flexibility over the distal section 1088 (or less tightly wound section). For example, the reinforcing element 1084 may be configured to provide a pushable structure resistant to collapse while still allowing the distal holding section 1046 to flex and bend to facilitate retrieval of the device 10. As can be appreciated, the spacing of adjacent windings (pitch), the size, and/or shape of the braid 1084 may be varied to achieve the desired characteristics. For example, a braid having a larger pitch (greater distance between adjacent windings) may be more flexible than a similarly sized and shaped braid having a smaller pitch.

While the reinforcing element 1084 is described as embedded within the polymeric body 1045, it is contemplated that the distal holding section 1046 may be formed in other manners. For example, a polymeric jacket may be disposed along the inner and/or outer surface of the reinforcing element 1084. It is contemplated that a polymeric material may be extruded or heat shrunk over the reinforcing element 1084. These are just examples. In some instances, the polymeric body 1045 may be injection molded with the reinforcing element 1084. In some instances, the reinforcing element or braid 1084 may extend from an inner surface of the distal holding section 1046. This may create a helical or threaded path to engage a mating threaded region (not explicitly shown) on the implantable device 10.

In some instances, the distal holding section 1046 may include an additional reinforcing element (not explicitly shown) positioned adjacent to the distal tip 1047. The reinforcing element may have a "C" shape configured to allow the distal end region of the distal holding section 1046 to expand. For example, the body portion 1045 may include a fold of excess material adjacent to the reinforcing element to allow the distal end region to expand and accommodate an implantable device 10. In some instances, the additional reinforcing element may have a generally rectangular cross-section. In other instances, it is contemplated that the reinforcing element may have any cross-sectional shape desired, such as, but not limited to, square, circular, oval, polygonal, etc. The additional reinforcing element may be formed from a radiopaque material or be doped with a radiopaque material.

The materials that can be used for the various components of the delivery devices, such as delivery devices 100/200/ 300/400/500/600/700/800/900/1000 (and/or other delivery structures disclosed herein) and the various members disclosed herein may include those commonly associated with medical devices. For simplicity purposes, the following discussion makes reference the delivery devices 100/200/ 300/400/500/600/700/800/900/1000 and components of thereof. However, this is not intended to limit the devices and methods described herein, as the discussion may be applied to other similar delivery systems and/or components of delivery systems or devices disclosed herein.

The delivery devices 100/200/300/400/500/600/700/800/ 900/1000 and/or other components of the delivery systems may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the polymer can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about –60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the delivery devices 100/200/300/400/500/600/700/800/900/1000 and/or other components of the delivery systems may be doped with, made of, or otherwise include a radiopaque material. Radiopaque materials are understood to be materials capable of producing a relatively bright image on a fluoroscopy screen or another imaging technique during a medical procedure. This relatively bright image aids the user of the delivery devices 100/200/300/400/500/600/700/800/900/1000 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the delivery devices 100/200/300/400/500/600/700/800/900/1000 to achieve the same result.

In some embodiments, a degree of Magnetic Resonance Imaging (MRI) compatibility is imparted into the delivery devices 100/200/300/400/500/600/700/800/900/1000. For example, delivery devices 100/200/300/400/500/600/700/800/900/1000, or portions or components thereof, may be made of a material that does not substantially distort the image and create substantial artifacts (i.e., gaps in the image). Certain ferromagnetic materials, for example, may not be suitable because they may create artifacts in an MRI image. The delivery devices 100/200/300/400/500/600/700/800/900/1000, or portions thereof, may also include and/or be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A delivery device for delivering an implantable leadless pacing device, the delivery device comprising:
   a proximal section having an outer diameter;
   a distal holding section extending distally of a distal end of the proximal section, the distal holding section defining a cavity therein for receiving an implantable leadless pacing device and the distal holding section having an outer diameter greater than the outer diameter of the proximal section;
   wherein the distal holding section comprises a braided reinforcing element covered by a polymeric body;
   wherein a proximalmost end of the braided reinforcing element is disposed within the distal holding section.

2. The delivery device of claim 1, wherein the braided reinforcing element is embedded within the polymeric body.

3. The delivery device of claim 2, wherein the polymeric body of the distal holding section includes a body portion and a distal tip portion distal of the body portion, wherein the body portion comprises a first polymeric material having a first durometer hardness and the distal tip portion comprises a second polymeric material having a second durometer hardness less than the first durometer hardness of the first polymeric material.

4. The delivery device of claim 3, wherein the distal tip portion defines a rounded distally facing tissue contacting surface.

5. The delivery device of claim 2, wherein the polymeric body of the distal holding section includes an inner layer of material facing the cavity and an outer layer of material, wherein the inner layer of material is harder than the outer layer of material.

6. The delivery device of claim 2, wherein the braided reinforcing element comprises a plurality of braided wires.

7. The delivery device of claim 6, wherein the braided reinforcing element includes a proximal section and a distal section, wherein a pitch of the braided wires in the proximal section of the braided reinforcing element is different than a pitch of the braided wires in the distal section of the braided reinforcing element.

8. The delivery device of claim 7, wherein the pitch in the proximal section is smaller than the pitch in the distal section.

9. The delivery device of claim 7, wherein the braided reinforcing element further includes an intermediate section between the proximal and distal sections, wherein a pitch of the braided wires in the intermediate section is different than the pitch of the braided wires in at least one of the proximal and distal sections.

10. A delivery device for delivering an implantable leadless pacing device, the delivery device comprising:
    an elongate shaft having an outer diameter;
    a distal holding section fixed to a distal end of the elongate shaft, the distal holding section having an outer diameter greater than the outer diameter of the elongate shaft;
    a push member slidably disposed in a lumen of the elongate shaft;
    wherein the distal holding section defines a cavity therein for receiving an implantable leadless pacing device and a distal opening for expelling the implantable leadless pacing device therefrom;
    wherein the distal holding section includes a braided reinforcing element embedded within a polymeric body;
    wherein a proximalmost end of the braided reinforcing element is disposed within the distal holding section.

11. The delivery device of claim 10, wherein the polymeric body of the distal holding section includes a body portion and a distal tip portion distal of the body portion, wherein the body portion comprises a first polymeric material having a first durometer hardness and the distal tip portion comprises a second polymeric material having a second durometer hardness less than the first durometer hardness of the first polymeric material.

12. The delivery device of claim 11, wherein the distal tip portion defines a convex tissue contacting distal surface.

13. The delivery device of claim 10, wherein the polymeric body of the distal holding section includes an inner layer of material facing the cavity and an outer layer of material, wherein the inner layer of material is harder than the outer layer of material.

14. The delivery device of claim 10, wherein the braided reinforcing element comprises a plurality of braided wires.

15. The delivery device of claim 14, wherein the braided reinforcing element includes a proximal section and a distal section, wherein a pitch of the braided wires in the proximal section of the braided reinforcing element is different than a pitch of the braided wires in the distal section of the braided reinforcing element.

16. The delivery device of claim 15, wherein the pitch in the proximal section is smaller than the pitch in the distal section.

17. The delivery device of claim 15, wherein the braided reinforcing element further includes an intermediate section between the proximal and distal sections, wherein a pitch of the braided wires in the intermediate section is different than the pitch of the braided wires in at least one of the proximal and distal sections.

18. A delivery device for delivering an implantable leadless pacing device, the delivery device comprising:
    an elongate shaft having an outer diameter;
    a distal holding section fixed to a distal end of the elongate shaft, the distal holding section having an outer diameter greater than the outer diameter of the elongate shaft;
    a push member slidably disposed in a lumen of the elongate shaft;
    wherein the distal holding section defines a cavity therein for receiving an implantable leadless pacing device and a distal opening for expelling the implantable leadless pacing device therefrom;
    wherein the distal holding section includes a braided reinforcing element embedded within a polymeric body;
    wherein a proximal end of the braided reinforcing element is located distal of the distal end of the elongate shaft.

19. The delivery device of claim 18, wherein the polymeric body of the distal holding section includes a body portion and a distal tip portion distal of the body portion, wherein the body portion comprises a first polymeric material having a first durometer hardness and the distal tip portion comprises a second polymeric material having a second durometer hardness less than the first durometer hardness of the first polymeric material.

20. The delivery device of claim 19, wherein the distal tip portion defines an atraumatic distally facing tissue contacting surface having a convex curvature.

* * * * *